United States Patent
Wu et al.

(10) Patent No.: US 9,430,828 B2
(45) Date of Patent: Aug. 30, 2016

(54) CLOUD-BASED MEDICAL IMAGE PROCESSING SYSTEM WITH TRACKING CAPABILITY

(71) Applicant: TERARECON, INC., Foster City, CA (US)

(72) Inventors: Junnan Wu, Acton, MA (US); Robert James Taylor, San Francisco, CA (US); Gang Li, Acton, MA (US); Tiecheng Zhao, Concord, MA (US); Chunguang Jia, Acton, MA (US)

(73) Assignee: TERARECON, INC., Foster City, CA (US)

( * ) Notice: Subject to any disclaimer, the term of this patent is extended or adjusted under 35 U.S.C. 154(b) by 27 days.

(21) Appl. No.: 14/174,115

(22) Filed: Feb. 6, 2014

(65) Prior Publication Data

US 2014/0153808 A1   Jun. 5, 2014

Related U.S. Application Data

(63) Continuation of application No. 13/396,548, filed on Feb. 14, 2012, now Pat. No. 8,682,049.

(51) Int. Cl.
*G06T 7/00* (2006.01)
*G06F 19/00* (2011.01)
*G06Q 10/10* (2012.01)
*G06Q 50/22* (2012.01)

(52) U.S. Cl.
CPC ........... *G06T 7/0012* (2013.01); *G06F 19/321* (2013.01); *G06Q 10/103* (2013.01); *G06Q 50/22* (2013.01)

(58) Field of Classification Search
None
See application file for complete search history.

(56) References Cited

U.S. PATENT DOCUMENTS

2004/0078238 A1   4/2004   Thomas et al.
2004/0240624 A1   12/2004  Shiibashi et al.
(Continued)

FOREIGN PATENT DOCUMENTS

| EP | 1939785 A2 | 7/2008 |
|---|---|---|
| WO | WO 2008/060323 A2 | 5/2008 |
| WO | WO 2010/124850 | 11/2010 |

OTHER PUBLICATIONS

PCT/US2013/025984, International Preliminary Report on Patentability, Date of Mailing Aug. 28, 2014, 6 pages.
(Continued)

*Primary Examiner* — Jon Chang
(74) *Attorney, Agent, or Firm* — Blakely, Sokoloff, Taylor & Zafman LLP

(57) ABSTRACT

A cloud server receives a request for accessing medical image data from a client device, where the cloud server provides image processing services to users in image processing steps, resulting in image views. User privileges of a user are determined for accessing the medical image data. In response to receiving a command having a selection of an image view from the client device, the cloud server provides the medical image data based on the selected one or more image views. The user interactions of the user with the medical image data via the selected image views are tracked, including tracking how much time the user takes to complete a particular medical image processing step. The tracked user interactions are stored in a persistent storage, and an analysis is performed on the tracked user interactions stored in the persistent storage to determine an overall usage trend of the image views.

17 Claims, 21 Drawing Sheets

(56) References Cited

U.S. PATENT DOCUMENTS

| | | |
|---|---|---|
| 2005/0021377 A1 | 1/2005 | Dobbs et al. |
| 2005/0148849 A1 | 7/2005 | Heere et al. |
| 2005/0251006 A1* | 11/2005 | Dellis .............. G06F 19/321 600/407 |
| 2006/0139319 A1* | 6/2006 | Kariathungal et al. ....... 345/156 |
| 2006/0293922 A1* | 12/2006 | Seare .............. G06F 19/328 705/2 |
| 2008/0120141 A1* | 5/2008 | Kariathungal ........ G06F 3/013 705/3 |
| 2009/0041329 A1* | 2/2009 | Nordell .............. G06F 19/321 382/134 |
| 2009/0103789 A1 | 4/2009 | Danner et al. |
| 2009/0132279 A1* | 5/2009 | Yeluri ............................ 705/3 |
| 2009/0271788 A1* | 10/2009 | Holt et al. ..................... 718/100 |
| 2011/0096970 A1* | 4/2011 | Vija ............................ 382/131 |
| 2011/0153351 A1 | 6/2011 | Vesper et al. |
| 2011/0161215 A1* | 6/2011 | Reed .............. G06Q 10/06393 705/34 |
| 2011/0191767 A1* | 8/2011 | Pinsky et al. ................. 717/176 |
| 2012/0173317 A1 | 7/2012 | Kelley |
| 2014/0365244 A1* | 12/2014 | Lee et al. ........................ 705/3 |

OTHER PUBLICATIONS

European Patent Application No. 13749291.4, Extended European Search Report, Dated Dec. 22, 2014, 6 pages.

* cited by examiner

FIG. 11

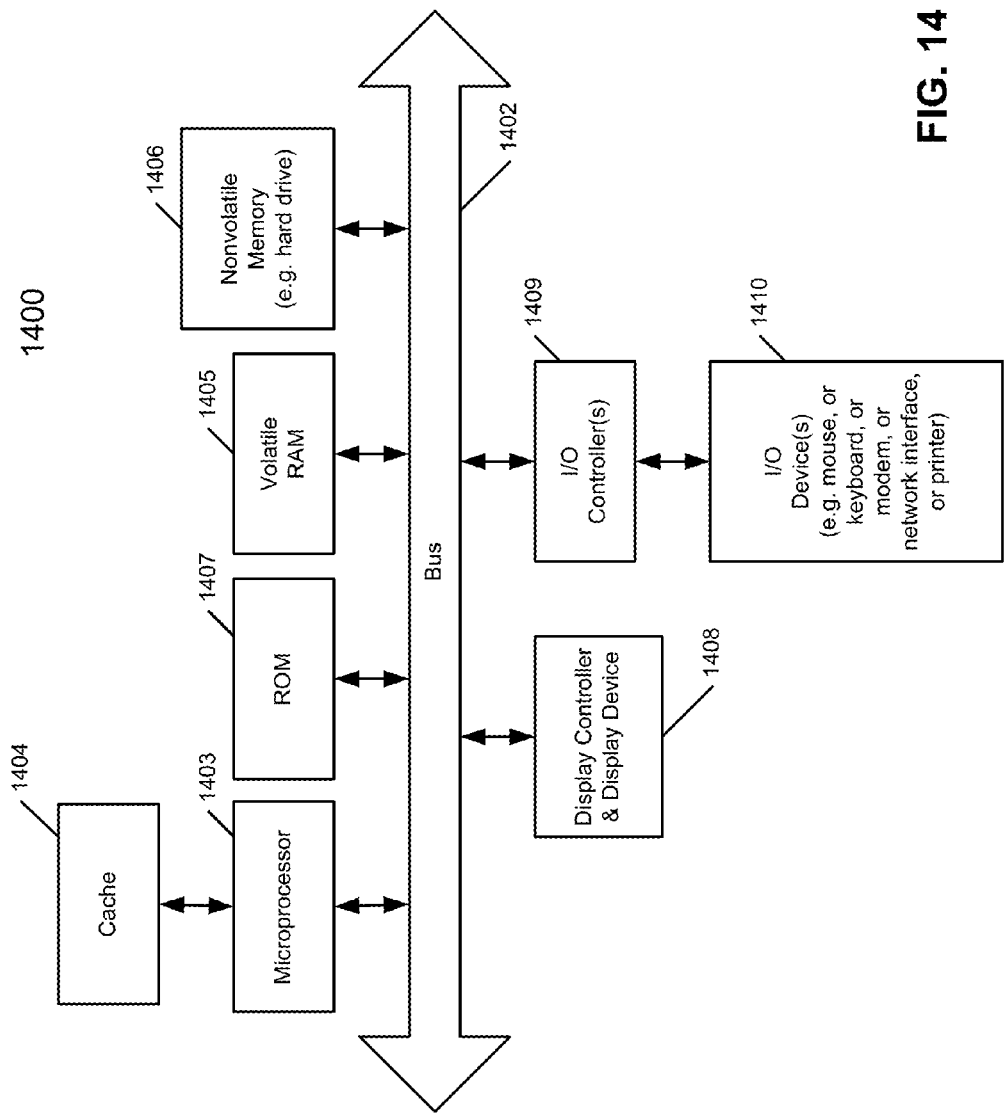

CLOUD-BASED MEDICAL IMAGE PROCESSING SYSTEM WITH TRACKING CAPABILITY

RELATED APPLICATIONS

This application is a continuation application of U.S. patent application Ser. No. 13/396,548, filed Feb. 14, 2012, which is incorporated by reference herein in its entirety.

FIELD OF THE INVENTION

Embodiments of the present invention relate generally to image processing systems. More particularly, embodiments of the invention relate to cloud-based medical image processing systems with tracking capability.

BACKGROUND

A computerized axial tomography scan (commonly known as a CAT scan or a CT scan) is an x-ray procedure, which combines many x-ray images with the aid of a computer to generate cross-sectional views of the internal organs and structures of the body. In each of these views, the body image is seen as an x-ray "slice" of the body. Typically, parallel slices are taken at different levels of the body, i.e., at different axial (z-axis) positions. This recorded image is called a tomogram, and "computerized axial tomography" refers to the recorded tomogram "sections" at different axial levels of the body. In multislice CT, a two-dimensional (2D) array of detector elements replaces the linear array of detectors used in conventional CT scanners. The 2D detector array permits the CT scanner to simultaneously obtain tomographic data at different slice locations and greatly increases the speed of CT image acquisition. Multislice CT facilitates a wide range of clinical applications, including three-dimensional (3D) imaging, with a capability for scanning large longitudinal volumes with high z-axis resolution.

Magnetic resonance imaging (MRI) is another method of obtaining images of the interior of objects, especially the human body. More specifically, MRI is a non-invasive, non-x-ray diagnostic technique employing radio-frequency waves and intense magnetic fields to excite molecules in the object under evaluation. Like a CAT scan, MRI provides computer-generated image "slices" of the body's internal tissues and organs. As with CAT scans, MRI facilitates a wide range of clinical applications, including 3D imaging, and provides large amounts of data by scanning large volumes with high resolution.

Medical image data, which are collected with medical imaging devices, such as X-ray devices, MRI devices, Ultrasound devices, Positron Emission Tomography (PET) devices or CT devices in the diagnostic imaging departments of medical institutions, are used for an image interpretation process called "reading" or "diagnostic reading." After an image interpretation report is generated from the medical image data, the image interpretation report, possibly accompanied by representative images or representations of the examination, are sent to the requesting physicians. Today, these image interpretation reports are usually digitized, stored, managed and distributed in plain text in a Radiology Information System (RIS) with accompanying representative images and the original examination stored in a Picture Archiving Communication System (PACS) which is often integrated with the RIS.

Typically, prior to the interpretation or reading, medical images may be processed or rendered using a variety of imaging processing or rendering techniques. Recent developments in multi-detector computed tomography (MDCT) scanners and other scanning modalities provide higher spatial and temporal resolutions than the previous-generation scanners.

Advanced image processing was first performed using computer workstations. However, there are several limitations to a workstation-based advanced image processing system. The hardware and software involved with these systems are expensive, and require complicated and time consuming installations. Because the workstation can only reside in one location, users must physically go to the workstation to use the advanced image processing software and tools. Also, only one person can use the workstation at a time.

Some have improved on this system by converting the workstation-based advanced image processing system to a client-server-based system. These systems offer some improvements over the workstation-based systems in that a user can use the client remotely, meaning the user does not have to be physically located near the server, but can use his/her laptop or computer elsewhere to use the software and tools for advanced image processing. Also, more than one client can be used with a given server at one time. This means that more than one user can simultaneously and remotely use the software that is installed on one server. The computational power of the software in a client-server-based system is distributed between the server and the client. In a "thin client" system, the majority of the computational capabilities exist at the server. In a "thick client" system, more of the computational capabilities, and possibly data, exist on the client.

The hardware software installation and maintenance costs and complexity of a client-server based system are still drawbacks. Also, there can be limitations on the number of simultaneous users that can be accommodated. Hardware and software must still be installed and maintained. Generally the information technology (IT) department of the center which purchased the system must be heavily involved, which can strain resources and complicate the installation and maintenance process.

BRIEF DESCRIPTION OF THE DRAWINGS

Embodiments of the invention are illustrated by way of example and not limitation in the figures of the accompanying drawings in which like references indicate similar elements.

FIG. 11 is a screenshot illustrating examples of GUIs for configuring anonymous data gateway management according to certain embodiments of the invention.

FIG. 14 is a block diagram of a data processing system, which may be used with one embodiment of the invention.

DETAILED DESCRIPTION

Figure 1A:
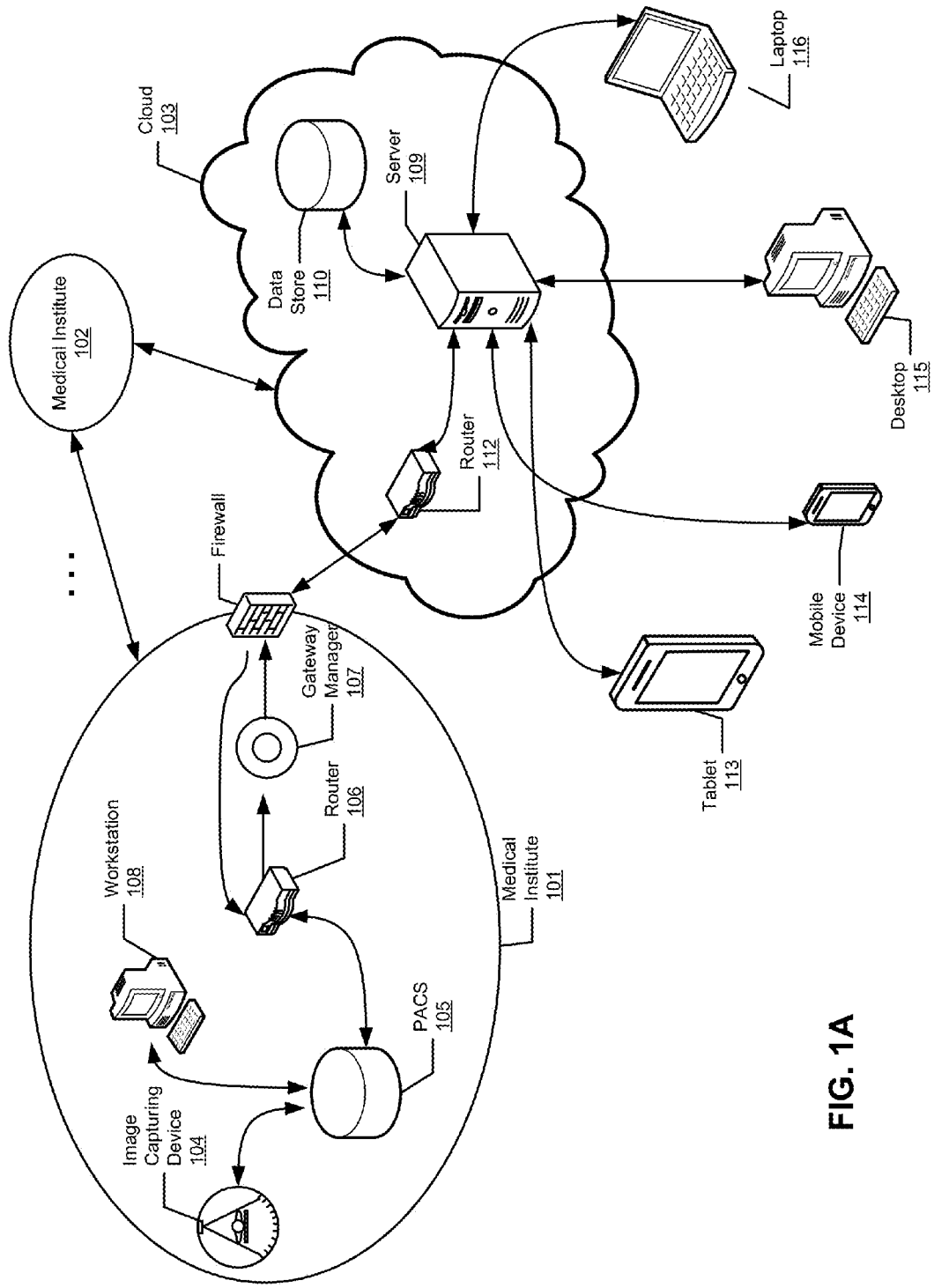
FIGS. 1A and 1B are block diagrams illustrating a cloud-based image processing system according to certain embodiments of the invention.

Various embodiments and aspects of the inventions will be described with reference to details discussed below, and the accompanying drawings will illustrate the various embodiments. The following description and drawings are illustrative of the invention and are not to be construed as limiting the invention. Numerous specific details are described to provide a thorough understanding of various embodiments of the present invention. However, in certain instances, well-known or conventional details are not described in order to provide a concise discussion of embodiments of the present inventions.

Reference in the specification to "one embodiment" or "an embodiment" means that a particular feature, structure, or characteristic described in conjunction with the embodiment can be included in at least one embodiment of the invention. The appearances of the phrase "in one embodiment" in various places in the specification do not necessarily all refer to the same embodiment.

According to some embodiments, advanced image processing systems are provided as cloud-based systems, particularly, for processing medical images. According to one embodiment, a cloud server is configured to provide advanced image processing services to a variety of clients, such as physicians from medical institutes, sole practitioners, agents from insurance companies, patients, medical researchers, regulating bodies, etc. A cloud server, also referred to as an image processing server, has the capability of processing one or more medical images to allow multiple participants to view and process the images either independently or in a collaborated manner or conferencing environment. Different participants may participate in different stages of a discussion session or a workflow process of the images. Dependent upon the privileges associated with their roles (e.g., doctors, insurance agents, patients, or third party data analysts or researchers), different participants may be limited to access only a portion of information relating to the images or a subset of the processing tools without compromising the privacy of the patients associated with the images.

According to some embodiments, a cloud-based medical image processing system includes a data gateway manager to automatically and/or manually transfer medical data to/from data providers such as medical institutes. Such data gateway management may be performed based on a set of rules or policies, which may be configured by an administrator or authorized personnel. In one embodiment, in response to updates to medical image data during an image discussion session or image processing operations performed at the cloud, the data gateway manager is configured to transmit over a network (e.g., Internet or intranet) the updated image data or data representing the difference between the updated image data and the original image data to a data provider that provided the original medical images. Similarly, the data gateway manager may be configured to transfer any new images from the data provider and store them in a data store of the cloud-based system. In addition, the data gateway manager may further transfer data amongst multiple data providers that are associated with the same entity (e.g., multiple facilities of a medical institute). Furthermore, the cloud-based system may automatically perform certain image pre-processing operations of the received images using certain advanced image processing resources provided by the cloud systems. The gateway manager may comprise a router, a computer, software or any combination of these components.

Figure 1B:
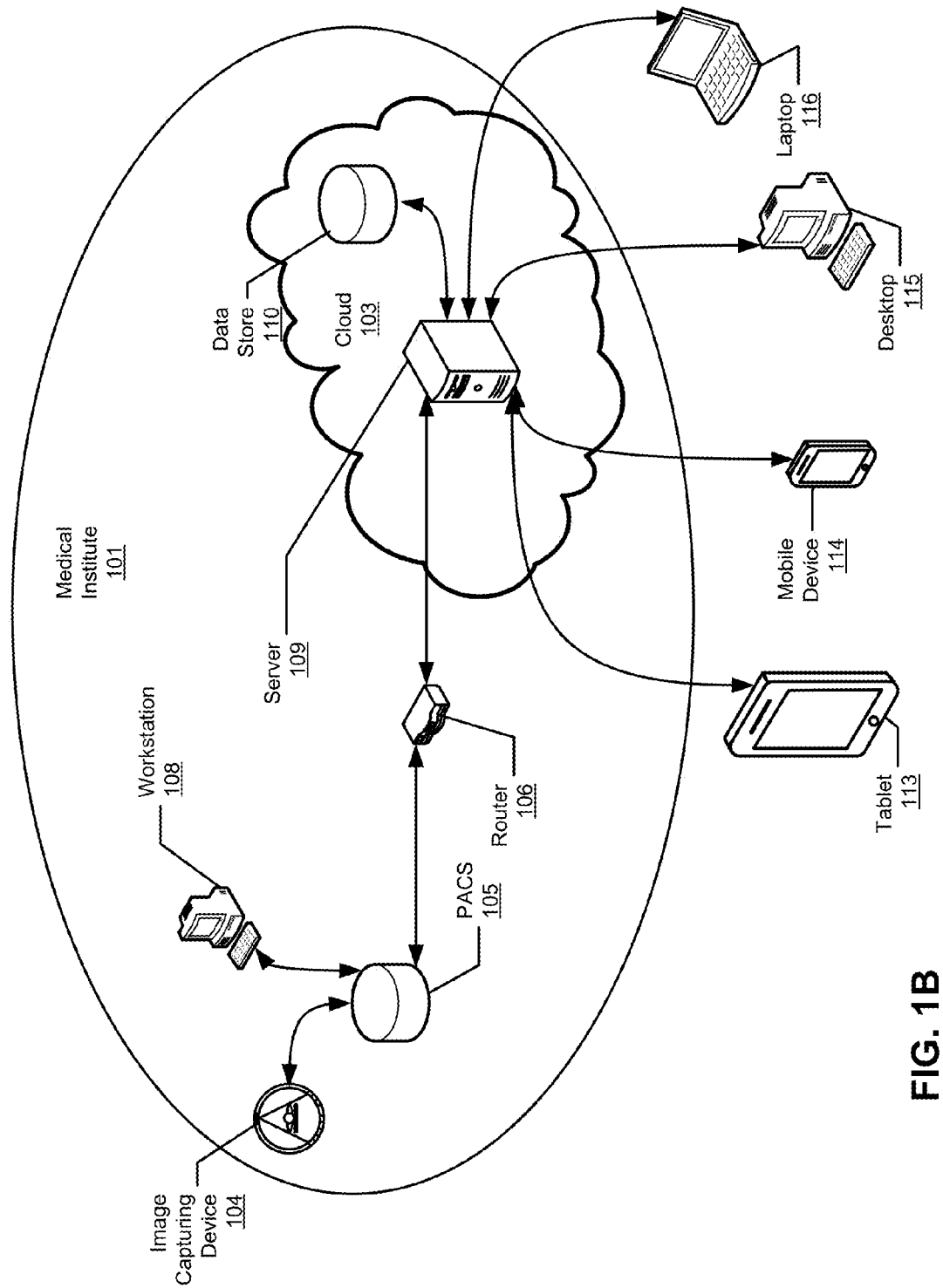

FIGS. 1A and 1B are block diagrams illustrating a cloud-based image processing system according to certain embodiments of the invention. Referring to FIG. 1A, according to one embodiment, system 100 includes one or more entities or institutes 101-102 communicatively coupled to cloud 103 over a network. Entities 101-102 may represent a variety of organizations such as medical institutes having a variety of facilities residing all over the world. For example, entity 101 may include or be associated with image capturing device or devices 104, image storage system (e.g., PACS) 105, router 106, and/or data gateway manager 107. Image storage system 105 may be maintained by a third party entity that provides archiving services to entity 101, which may be accessed by workstation 108 such as an administrator or user associated with entity 101. Note that throughout this application, a medical institute is utilized as an example of an organization entity. However, it is not so limited; other organizations or entities may also be applied.

In one embodiment, cloud 103 may represent a set of servers or clusters of servers associated with a service provider and geographically distributed over a network. For example, cloud 103 may be associated with a medical image processing service provider such as TeraRecon of Foster City, Calif. A network may be a local area network (LAN), a metropolitan area network (MAN), a wide area network (WAN) such as the Internet or an intranet, or a combination thereof. Cloud 103 can be made of a variety of servers and devices capable of providing application services to a variety of clients such as clients 113-116 over a network. In one embodiment, cloud 103 includes one or more cloud servers 109 to provide image processing services, one or more databases 110 to store images and other medical data, and one or more routers 112 to transfer data to/from other entities such as entities 101-102. If the cloud server consists of a server cluster, or more than one server, rules may exist which control the transfer of data between the servers in the cluster. For example, there may be reasons why data on a server in one country should not be placed on a server in another country.

Server 109 may be an image processing server to provide medical image processing services to clients 113-116 over a network. For example, server 109 may be implemented as part of a TeraRecon AquariusNET™ server and/or a TeraRecon AquariusAPS server. Data gateway manager 107 and/or router 106 may be implemented as part of a TeraRecon AquariusGATE device. Medical imaging device 104 may be an image diagnosis device, such as X-ray CT device, MRI scanning device, nuclear medicine device, ultrasound device, or any other medical imaging device. Medical imaging device 104 collects information from multiple cross-section views of a specimen, reconstructs them, and produces medical image data for the multiple cross-section views. Medical imaging device 104 is also referred to as a modality.

Database 110 may be a data store to store medical data such as digital imaging and communications in medicine (DICOM) compatible data or other image data. Database 110 may also incorporate encryption capabilities. Database 110 may include multiple databases and/or may be maintained by a third party vendor such as storage providers. Data store 110 may be implemented with relational database management systems (RDBMS), e.g., Oracle™ database or Microsoft® SQL Server, etc. Clients 113-116 may represent a variety of client devices such as a desktop, laptop, tablet, mobile phone, personal digital assistant (PDA), etc. Some of clients 113-116 may include a client application (e.g., thin client application) to access resources such as medical image processing tools or applications hosted by server 109 over a network. Examples of thin clients include a web browser, a phone application and others.

According to one embodiment, server 109 is configured to provide advanced image processing services to clients 113-116, which may represent physicians from medical institutes, agents from insurance companies, patients, medical researchers, etc. Cloud server 109, also referred to as an image processing server, has the capability of hosting one or more medical images and data associated with the medical images to allow multiple participants such as clients 113-116, to participate in a discussion/processing forum of the images in a collaborated manner or conferencing environment. Different participants may participate in different stages and/or levels of a discussion session or a workflow process of the images. Dependent upon the privileges associated with their roles (e.g., doctors, insurance agents, patients, or third party data analysts or researchers), different participants may be limited to access only a portion of the information relating to the images or a subset of the tools and functions without compromising the privacy of the patients associated with the images.

According to some embodiments, data gateway manager 107 is configured to automatically or manually transfer medical data to/from data providers (e.g., PACS systems) such as medical institutes. Such data gateway management may be performed based on a set of rules or policies, which may be configured by an administrator or authorized personnel. In one embodiment, in response to updates of medical images data during an image discussion session or image processing operations performed in the cloud, the data gateway manager is configured to transmit over a network (e.g., Internet) the updated image data or the difference between the updated image data and the original image data to a data provider such as PACS 105 that provided the original medical image data. Similarly, data gateway manager 107 can be configured to transmit any new images and/or image data from the data provider, where the new images may have been captured by an image capturing device such as image capturing device 104 associated with entity 101. In addition, data gateway manager 107 may further transfer data amongst multiple data providers that is associated with the same entity (e.g., multiple facilities of a medical institute). Furthermore, cloud 103 may include an advanced preprocessing system (not shown) to automatically perform certain pre-processing operations of the received images using certain advanced image processing resources provided by the cloud systems. In one embodiment, gateway manager 107 is configured to communicate with cloud 103 via certain Internet ports such as port 80 or 443, etc. The data being transferred may be encrypted and/or compressed using a variety of encryption and compression methods. The term "Internet port" in this context could also be an intranet port, or a private port such as port 80 or 443 etc. on an intranet.

Thus, using a cloud-based system for advanced image processing has several advantages. A cloud system refers to a system which is server-based, and in which the software clients are very thin—possibly just a web browser, a web browser with a plug-in, or a mobile or phone application, etc. The server or server cluster in the cloud system is very powerful computationally and can support several users simultaneously. The server may reside anywhere and can be managed by a third party so that the users of the software in the cloud system do not need to concern themselves with software and hardware installation and maintenance.

A cloud system also allows for dynamic provisioning. For example, if facility X needs to allow for a peak of 50 users, they currently need a 50 user workstation or client-server system. If there are 10 such facilities, then a total of 500 users must be provided for with workstations, or client-server equipment, IT staff, etc. Alternatively, if these same facilities use a cloud service, and for example, the average number of simultaneous users at each place is 5 users, then the cloud service only needs to provide enough resource to handle the average (5 simultaneous users) plus accommodations for some peaks above that. For the 10 facilities, this would mean 50 simultaneous users to cover the average and conservatively 100 simultaneous users to cover the peaks in usage. This equates to a 150-user system on the cloud system vs. a 500-user system using workstations or a client-server model, resulting in a 70% saving in cost of equipment and resources etc. This allows lower costs and removes the need for the individual sites to have to manage the asset.

Cloud computing provides computation, software, data access, and storage services that do not require end-user knowledge of the physical location and configuration of the system that delivers the services. Cloud computing providers deliver applications via the Internet, which are accessed from Web browsers, desktop and mobile apps, while the business software and data are stored on servers at a remote location. Cloud application services deliver software as a service over the Internet, eliminating the need to install and run the application on the customer's own computers and simplifying maintenance and support.

A cloud system can be implemented in a variety of configurations. For example, a cloud system can be a public cloud system as shown in FIG. 1A, a community cloud system, a hybrid cloud system, a private cloud system as shown in FIG. 1B, or a combination thereof. Public cloud describes cloud computing in the traditional mainstream sense, whereby resources are dynamically provisioned to the general public on a self-service basis over the Internet, via Web applications/Web services, or other internet services, from an off-site third-party provider who bills on a utility computing basis. Community cloud shares infrastructure between several organizations from a specific community with common concerns (security, compliance, jurisdiction, etc.), whether managed internally or by a third-party and hosted internally or externally. The costs are spread over fewer users than a public cloud (but more than a private cloud), so only some of the benefits of cloud computing are realized. Hybrid cloud is a composition of two or more clouds (private, community, or public) that remain unique entities but are bound together, offering the benefits of multiple deployment models. Briefly it can also be defined as a multiple cloud systems which are connected in a way that allows programs and data to be moved easily from one deployment system to another. Private cloud is infrastructure operated solely for a single organization, whether managed internally or by a third-party and hosted internally or externally. Generally, access to a private cloud is limited to that single organization or its affiliates.

With cloud computing, users of clients such as clients 113-116 do not have to maintain the software and hardware associated with the image processing. The users only need to pay for usage of the resources provided from the cloud as and when they need them, or in a defined arrangement, such as a monthly or annual contract. There is minimal or no setup and users can sign up and use the software immediately. In some situations, there may be a small software installation, like a Citrix or java or plug-in. Such a configuration lowers up-front and maintenance costs for the users and there is no or lower hardware, software, or maintenance costs. The cloud servers can handle backups and redundancies and security so the users do not have to worry about these issues. The users can have access to all and the newest clinical software without having to install the same. Tools and software are upgraded (automatically or otherwise) at the servers to the latest versions. Access to tools is driven by access level, rather than by software limitations. Cloud servers can have greater computational power to preprocess and process images and they can be larger and more powerful with better backup, redundancy, security options. For example, a cloud server can employ volume rendering techniques available from TeraRecon to render large volume of medical images. Further detailed information concerning the volume rendering techniques can be found in U.S. Pat. Nos. 6,008,813 and 6,313,841, which are incorporated by reference herein.

According to one embodiment, image processing services provided by cloud 103 can be provided based on a variety of licensing models, such as, for example, based on the number of users, case uploads (e.g., number of cases, number of images or volume of image data), case downloads (e.g., number of cases, number of images or volume of image data), number of cases processed and/or viewed, image processing requirements, type of user (e.g., expert, specialty or general user), by clinical trial or by research study, type of case, bandwidth requirements, processing power/speed requirements, priority to processing power/speed (e.g., system in ER may pay for higher priority), reimbursement or billing code (e.g., user may only pay to perform certain procedures that are reimbursed by insurance), time using software (e.g., years, months, weeks, days, hours, even minutes), time of day using software, number of concurrent users, number of sessions, or any combination thereof.

Figure 2:
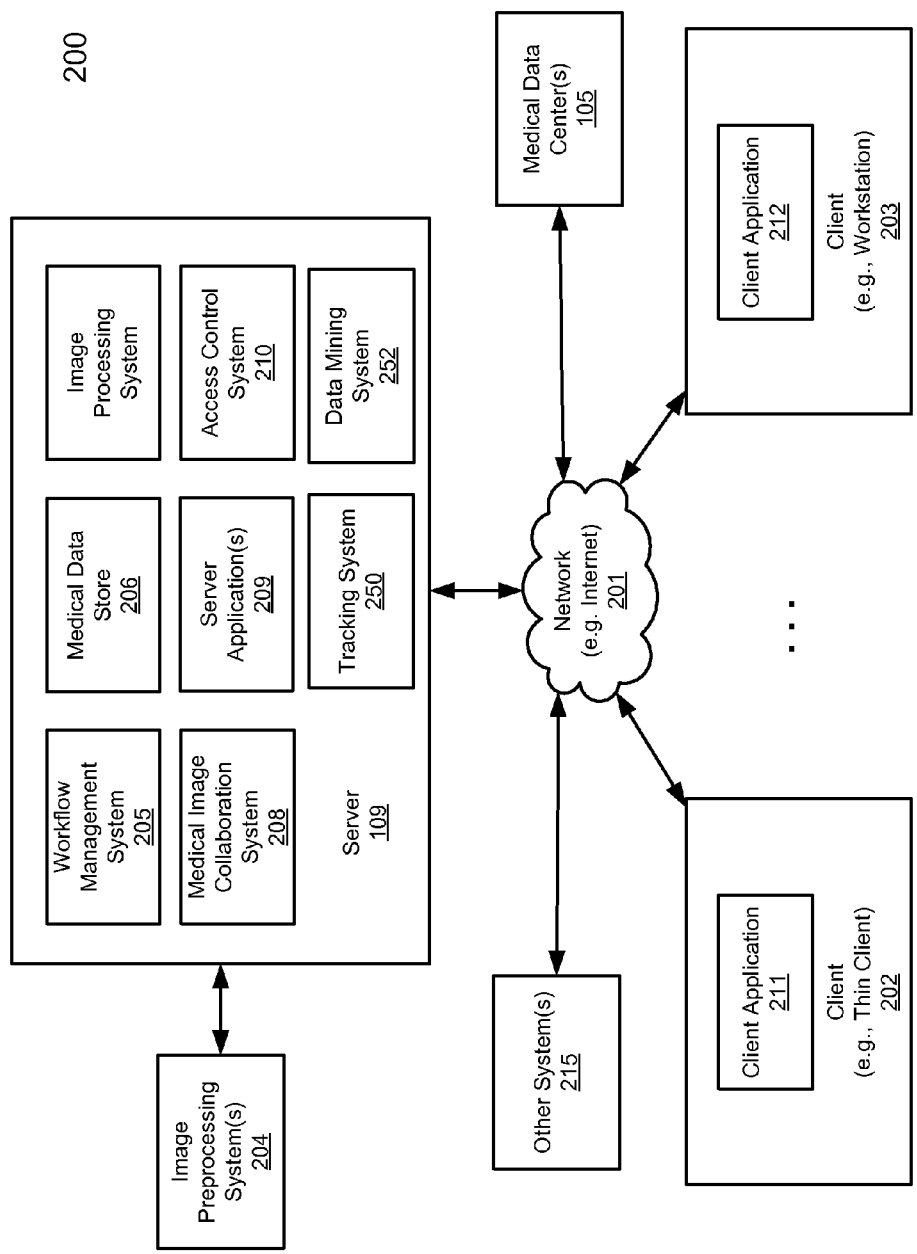
FIG. 2 is a block diagram illustrating a cloud-based image processing system according to another embodiment of the invention.

FIG. 2 is a block diagram illustrating a cloud-based image processing system according to another embodiment of the invention. For example, system 200 may be implemented as part of the system as shown in FIGS. 1A and 1B. Referring to FIG. 2, system 200 includes server 109 communicatively coupled to one or more clients 202-203 over network 201, which may be a LAN, MAN, WAN, or a combination thereof. Server 109 is configured to provide cloud-based image processing services to clients 202-203 based on a variety of usage licensing models. Each of clients 202-203 includes a client application such as client applications 211-212 to communicate with a server counterpart 209, respectively, to access resources provided by server 109. Server application 209 may be implemented as a virtual server or instance of the server application 209, one for each client.

According to one embodiment, server 109 includes, but is not limited to, workflow management system 205, medical data store 206, image processing system 207, medical image collaboration system 208, and access control system 210. Medical data store 206 may be implemented as part of database 110 of FIGS. 1A and 1B. Medical data store 206 is utilized to store medical images and image data received from medical data center (e.g., PACS systems) 105 or other image storage systems 215 (e.g., CD-ROMs, or hard drives) and processed by image processing system 207 and/or image preprocessing systems 204. Image processing system 207 includes a variety of medical imaging processing tools or applications that can be invoked and utilized by clients 202-203 via their respective client applications 211-212, respectively, according to a variety of licensing terms or agreements. It is possible that in some medical institutes that the image storage system 215 and the image capturing device 104 may be combined.

In response to image data received from medical data center 105 or from image capturing devices (not shown) or from another image source, such as a CD or computer desktop, according to one embodiment, image preprocessing system 204 may be configured to automatically perform certain preprocesses of the image data and store the preprocessed image data in medical data store 206. For example, upon receipt of image data from PACS 105 or directly from medical image capturing devices, image preprocessing system 204 may automatically perform certain operations, such as bone removal, centerline extraction, sphere finding, registration, parametric map calculation, reformatting, time-density analysis, segmentation of structures, and auto-3D operations, and other operations. Image preprocessing system 204 may be implemented as a separate server or alternatively, it may be integrated with server 109. Furthermore, image preprocessing system 204 may perform image data preprocesses for multiple cloud servers such as server 109.

In one embodiment, a client/server image data processing architecture is installed on system 200. The architecture includes client partition (e.g., client applications 211-212) and server partition (e.g., server applications 209). The server partition of system 200 runs on the server 109, and communicates with its client partition installed on clients 202-203, respectively. In one embodiment, server 109 is distributed and running on multiple servers. In another embodiment, the system is a Web-enabled application operating on one or more servers. Any computer or device with Web-browsing application installed may access and utilize the resources of the system without any, or with minimal, additional hardware and/or software requirements.

In one embodiment, server 109 may operate as a data server for medical image data received from medical image capturing devices. The received medical image data is then stored into medical data store 206. In one embodiment, for example, when client 202 requests for unprocessed medical image data, server application 209 retrieves the data from the medical data store 206 and renders the retrieved data on behalf of client 202.

Image preprocessing system 204 may further generate workflow information to be used by workflow management system 205. Workflow management system 205 may be a separate server or integrated with server 109. Workflow management system 205 performs multiple functions according to some embodiments of the invention. For example, workflow management system 205 performs a data server function in acquiring and storing medical image data received from the medical image capturing devices. It may also act as a graphic engine or invoke image processing system 207 in processing the medical image data to generate 2D or 3D medical image views.

In one embodiment, workflow management system 205 invokes image processing system 207 having a graphics engine to perform 2D and 3D image generating. When a client (e.g., clients 202-203) requests for certain medical image views, workflow management system 205 retrieves medical image data stored in medical data store 206, and renders 2D or 3D medical image views from the medical image data. The end results for medical image views are sent to the client.

In one embodiment, when a user making adjustments to the medical image views received from server 109, these user adjustment requests are sent back to the workflow management system 205. Workflow management system 205 then performs additional graphic processing based on the user requests, and the newly generated, updated medical image views are returned to the client. This approach is advantageous because it eliminates the need to transport large quantity of unprocessed medical image data across network, while providing 2D or 3D image viewing to client computers with minimal or no 2D or 3D image processing capacity.

As described above, when implemented as a cloud based application, system 200 includes a client-side partition and a server-side partition. Functionalities of system 200 are distributed to the client-side or server-side partitions. When a substantial amount of functionalities are distributed to the client-side partition, system 200 may be referred to as a "thick client" application. Alternatively, when a limited amount of functionalities are distributed to the client-side partition, while the majority of functionalities are performed by the server-side partition, system 200 may be referred to as a "thin client" application. In another embodiment, functionalities of system 200 may be redundantly distributed both in client-side and server-side partitions. Functionalities may include processing and data. Server 109 may be implemented as a web server. The web server may be a third-party web server (e.g., Apache™ HTTP Server, Microsoft® Internet Information Server and/or Services, etc).

In one embodiment, workflow management system 205 manages the creation, update and deletion of workflow templates. It also performs workflow scene creation when receiving user requests to apply a workflow template to medical image data. A workflow is defined to capture the repetitive pattern of activities in the process of generating medical image views for diagnosis. A workflow arranges these activities into a process flow according to the order of performing each activity. Each of the activities in the workflow has a clear definition of its functions, the resource required in performing the activity, and the inputs received and outputs generated by the activity. Each activity in a workflow is referred to as a workflow stage, or a workflow element. With requirements and responsibilities clearly defined, a workflow stage of a workflow is designed to perform one specific task in the process of accomplishing the goal defined in the workflow. For many medical image studies, the patterns of activities to produce medical image views for diagnosis are usually repetitive and clearly defined. Therefore, it is advantageous to utilize workflows to model and document real life medical image processing practices, ensuring the image processing being properly performed under the defined procedural rules of the workflow. The results of the workflow stages can be saved for later review or use.

In one embodiment, a workflow for a specific medical image study is modeled by a workflow template. A workflow template is a template with a predefined set of workflow stages forming a logical workflow. The order of processing an activity is modeled by the order established among the predefined set of workflow stages. In one embodiment, workflow stages in a workflow template are ordered sequentially, with lower order stages being performed before the higher order stages. In another embodiment, dependency relationships are maintained among the workflow stages. Under such arrangement, a workflow stage cannot be performed before the workflow stages it is depending on being performed first. In a further embodiment, advanced workflow management allows one workflow stage depending on multiple workflow stages, or multiple workflow stages depending on one workflow stage, etc.

The image processing operations receive medical image data collected by the medical imaging devices as inputs, process the medical image data, and generate metadata as outputs. Metadata, also known as metadata elements, broadly refers to parameters and/or instructions for describing, processing, and/or managing the medical image data. For instance, metadata generated by the image processing operations of a workflow stage includes image processing parameters that can be applied to medical image data to generate medical image views for diagnostic purpose. Further, various automatic and manual manipulations of the medical image views can also be captured as metadata. Thus, metadata allows the returning of the system to the state it was in when the metadata was saved.

After a user validates the results generated from processing a workflow stage predefined in the workflow template, workflow management system 205 creates a new scene and stores the new scene to the workflow scene. Workflow management system 205 also allows the updating and saving of scenes during user adjustments of the medical image views generated from the scenes. Further detailed information concerning workflow management system 205 can be found in co-pending U.S. patent application Ser. No. 12/196,099, entitled "Workflow Template Management for Medical Image Data Processing," filed Aug. 21, 2008, which is incorporated by reference herein in its entirety.

Figure 3B:
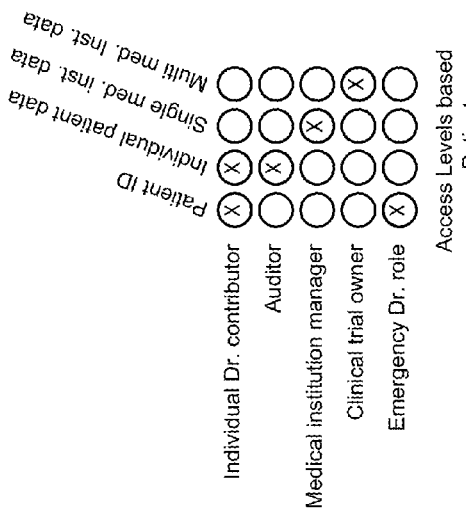
FIGS. 3A-3D are diagrams illustrating examples of access control data structures according to certain embodiments of the invention.
Figure 3D:
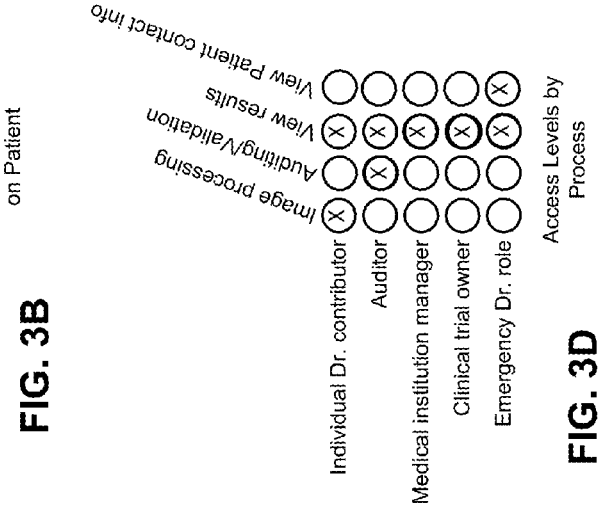
Figure 3A:
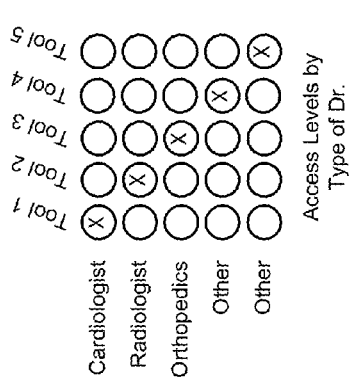
Figure 3C:
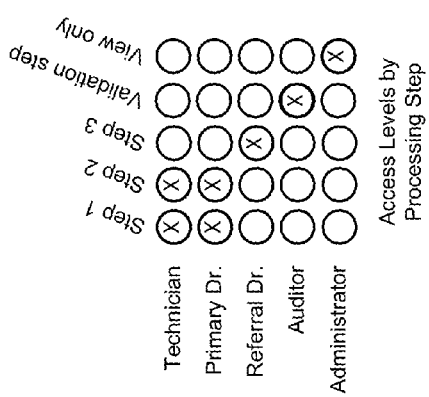

Referring back to FIG. 2, according to one embodiment, server 109 further includes access control system 210 to control access of resources (e.g., image processing tools) and/or medical data stored in medical data store 206 from clients 202-203. Clients 202-203 may or may not access certain portions of resources and/or medicate data stored in medical data store 206 dependent upon their respective access privileges. The access privileges may be determined or configured based on a set of role-based rules or policies, as shown in FIGS. 3A-3D. For example, some users with certain roles can only access some of the tools provided by the system as shown in FIG. 3A. Examples of some of the tools available are listed at the end of this document, and include vessel centerline extraction, calcium scoring and others. Some users with certain roles are limited to some patient information as shown in FIG. 3B. Some users with certain roles can only perform certain steps or stages of the medical image processes as shown in FIG. 3C. Steps or stages are incorporated into the tools (listed at the end of this document) and might include identifying and/or measuring instructions, validation of previously performed steps or stages and others. Some users with certain roles are limited to certain types of processes as shown in FIG. 3D.

Note that the rules or policies as shown in FIGS. 3A-3D are described for the purpose of illustration only; other rules and formats may also be applied. According to some embodiments, access levels can be configured based on a variety of parameters, such as, for example, types of tools or steps within a tool, functions (e.g., uploading, downloading, viewing, manipulating, auditing, validating, etc.), ability to give others access (e.g., second opinion, referrals, experts, family, friend etc.), patients, volume (e.g., may only have access to certain volume of images/month for example, dependent upon a licensing agreement), medical institution, specialty, reimbursement or billing code (e.g., may only have access to perform certain procedures that are reimbursed by insurance), admin access level, clinical trial or research project, and way of viewing data—some may only be able to see individual patients, some aggregate data which can be sliced different ways, etc.

Figure 4A:
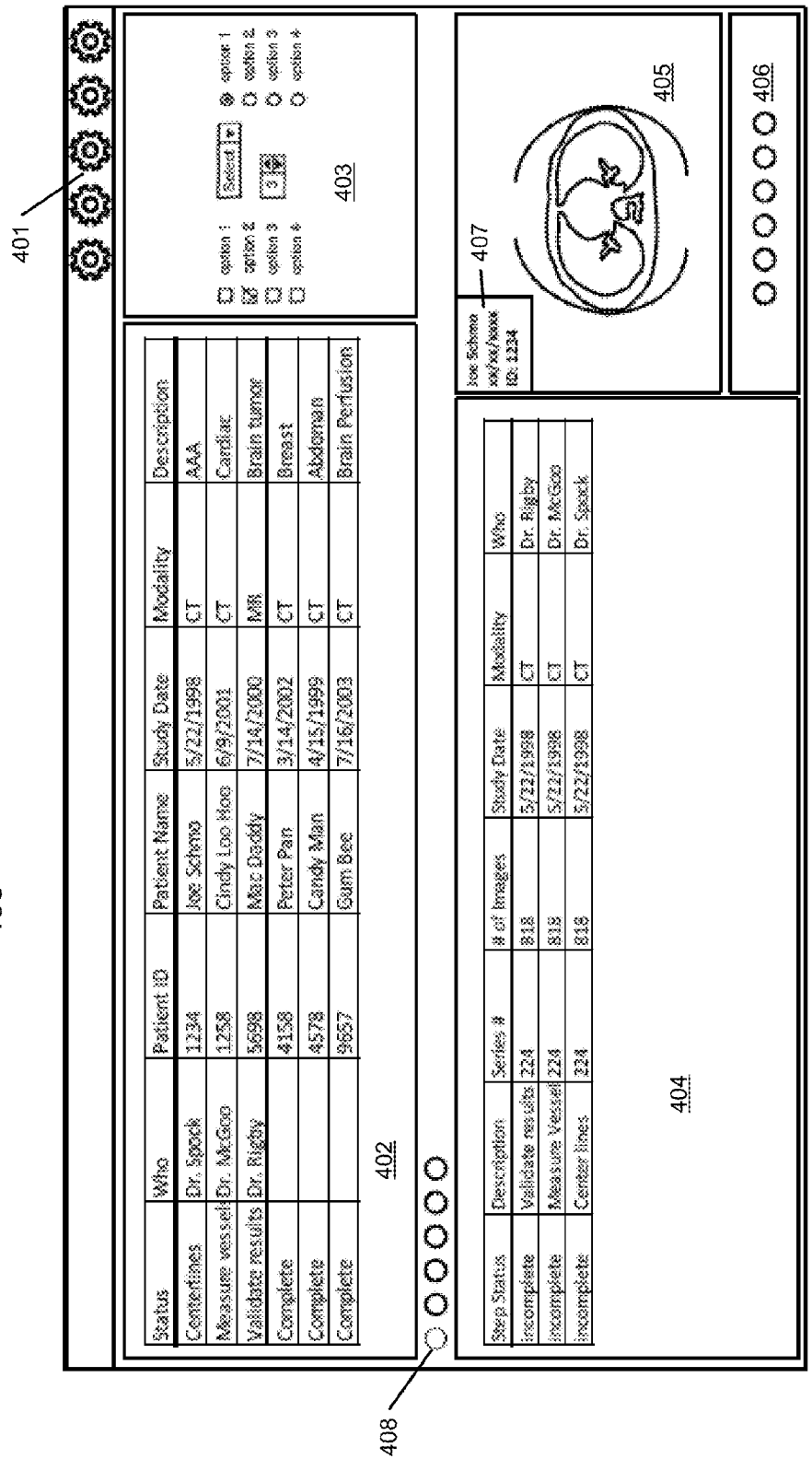
FIGS. 4A-4C are screenshots illustrating certain graphical user interfaces (GUIs) of a cloud-based image processing system according to one embodiment of the invention.
Figure 4B:
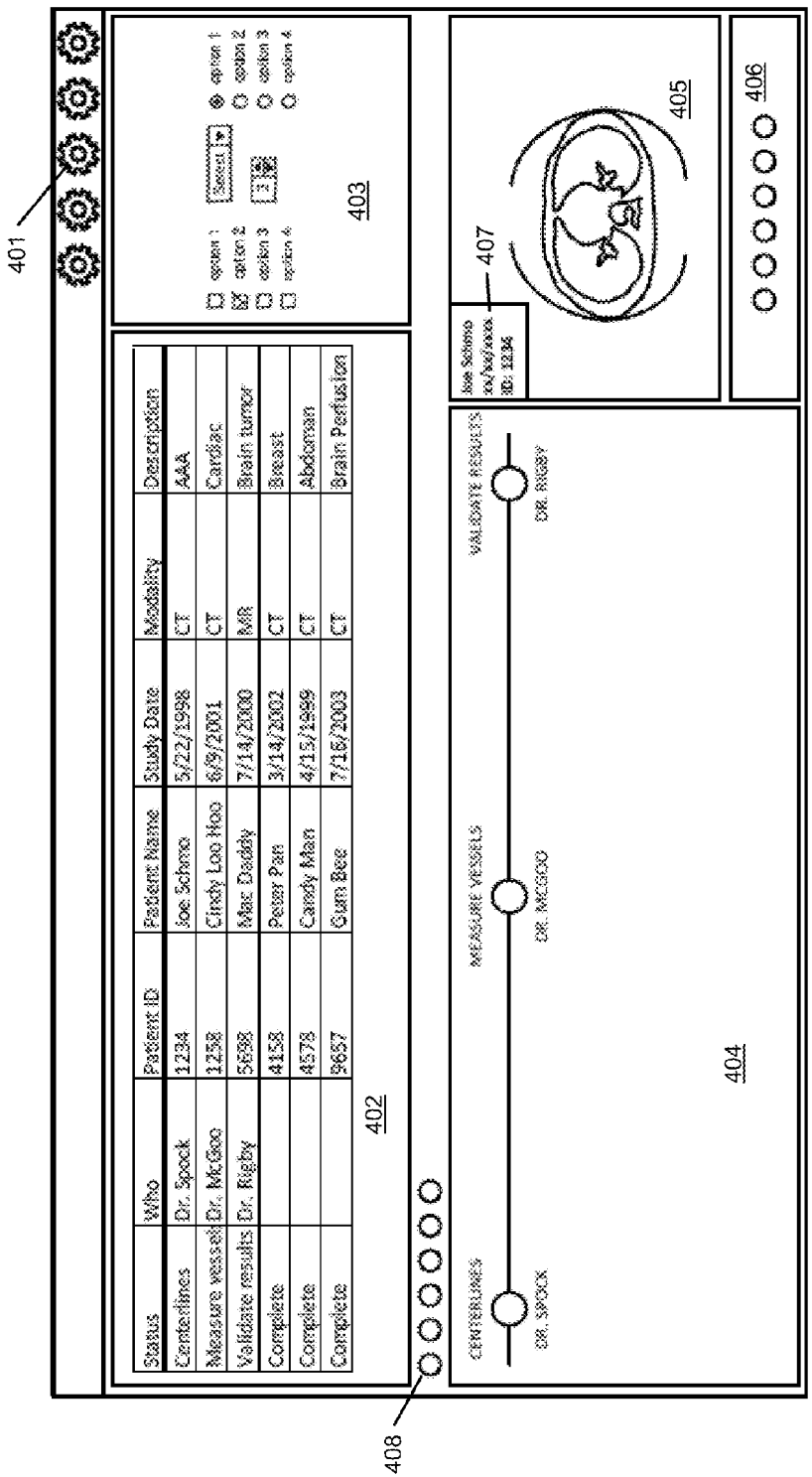

FIGS. 4A and 4B are screenshots illustrating certain graphical user interfaces (GUIs) of a cloud-based image processing system according to one embodiment of the invention. For example, GUI 400 of FIGS. 4A and 4B may be presented by workflow management system 205 at clients 202-203 as part of client applications 211-212 of FIG. 2. Referring to FIGS. 4A and 4B, GUI 400 includes one or more controls or buttons 401 to configure certain settings of the application, such as preferences, help and others. GUI 400 further includes display area 402 to display a certain patient study list, where the list may be obtained via a search that is configured based on one or more search options 403, such as by patient ID, patient name, date, modality or others. GUI 400 further includes display area 404 to display a list of tasks or workflows to be handled by different personnel. The task list may be presented as a table as shown in FIG. 4A or alternatively as a timeline as shown in FIG. 4B. GUI 400 further includes image preview area 405 to display a preview of an image of a particular patient in question, optionally including patient information 407 and a set of one or more imaging viewing tools 406, such as brightness, contrast and others. The availability of the patient information 407, certain detailed information of image preview 405, and tools 406 may be determined based on access privileges of a particular user, which may be controlled by access control system 210. Furthermore, GUI 400 further includes a set of one or more file management tools 408 for managing image files, such as import, load, send, upload, etc. Note that GUIs described throughout this application are shown for the purposes of illustration only; other formats or layouts may also be implemented. Certain GUI control or button can be activated via a variety of mechanisms, such as keyboard, keypad, touch screen, touch pad, PDA controls, phone controls, mouse click, an interactive voice command, or a combination thereof.

Referring back to FIG. 2, according to one embodiment, server 109 may further include a tracking system 250, which may be integrated with server 109 or alternatively maintained by a third party vendor and accessible by server 109. The tracking system 250 is configured to monitor and track user activities with respect to medical data stored in medical data store 206. Because of certain FDA requirements, there is a need to track what users have accessed the software, when, and the steps they have used within the software. There is also a need to track overall trends in software use, for example how long it takes a user to complete a certain type of case, or certain steps, billing trends etc. According to some embodiments, the tracking system 250 is configured to track users who log in and utilize the software, steps the users perform, date and time of the accesses, etc. The tracking system 250 can be used to analyze volumes used on, and performance of, the system. The tracking system 250 can be used to track FDA/HIPAA compliance. It can also be utilized by insurance companies to track billing codes and costs. It can be used to determine trends (time to analyze certain types of cases etc.) Analysis of tracked data can also be used to identify different user types, for example expert users, casual users, technicians, physicians, etc. This information can then be used to improve the software product, upsell, improve customer service, improve billing models, etc. The tracking system 250 can be used to track aggregate data as well as detailed data.

According to one embodiment, the browser/client/mobile application standards allow easier integration with an electronic health record. The integration can be done as seamless as possible, so one does not have to open separate applications or repeatedly enter login information. Integration may be based on patient ID, or other common parameter which automatically links different types of records. It can also be used to link anonymous cases to online publications—allowing 3D or advanced views of case images. The cloud-based system is flexible so it can adapt integration standards as they develop and as they evolve.

As described above, advanced image processing in the cloud model allows users from anywhere to access and contribute to the same case or cases. An extension of these concepts is a clinical or research trial. In a clinical or research trial, patient data from different geographical locations are grouped and tracked over time to identify trends. In the case of a clinical trial, the trends may be related to a particular treatment or drug. Advanced image processing is useful in tracking these trends. For example, a drug for cancer can be assessed by tracking patients with cancer who have taken the drug or a placebo. The software can be used to measure the size of the tumor, or other aspects of the patient, such as side effects. For example, a drug to treat liver cancer may have a potential adverse effect on the function of the heart or other organs. A clinical trial can use advanced image processing to track not only the health of the liver, but also the health of the heart and other organs over time.

The cloud model allows for doctors or other participants all over the world to participate. It controls what tools are used and how and by whom. It allows data to be aggregated because all data is stored on the same server or cluster of servers. It allows easier training for the doctors and technicians and others involved in analyzing data for clinical trial or research study. The cloud-based model easily supports the role of auditor/quality control person and supports an FDA or company oversight role. It monitors data trends as trial is progressing and performs data analysis at the end of a trial/study and also during a trial/study. It also integrates with data analysis software, giving access to third parties such as a sponsor or the FDA, and controls access and level of access.

Cloud-Based Medical Data Mining Services

The cloud based system as shown in FIG. 2 allows data from several different medical centers and geographies to be located on one server or one group of servers. Because the data is all in one place (geographically or virtually), the data can be combined and used in the aggregate. This aggregation can be for one patient, across patients, across time, or any combination of these. According to one embodiment, server 109 further includes a data mining 252 component or system (not shown) configured to perform data mining 252 on medical data received from a variety of data sources. The data mining system 252 may be integrated with server 109 or alternatively maintained by a third party service provider over a network and invoked by server 109. The data mining system 252 is configured to provide cloud-based data mining or analysis services on medical data stored in medical data store 206 to a variety of clients over the Internet. The data mining system 252 can perform a variety of mining and analysis operations on demand from a client, or automatically, and generate and deliver the results to the client based on a variety of service or licensing agreements.

Some of the reasons one would want to mine aggregated data relating to quantitative image processing include clinical trials, clinical research, trend identification, prediction of disease progress, diagnosis, artificial intelligence, and for use by insurance companies. Quantitative image processing refers to image processing that results in a value such as a measurement of a tumor diameter. According to one embodiment, the data mining system has the ability to do massive, anonymized, automatic, and continual analysis and trending on all the data from multiple sources. The data mining system can perform quantitative image data analysis that can be performed before a user requires the data (in the background, at night, etc.) The data mining system has the ability to access and use this information quickly and in real time since the user does not have to download all the images and then do the analysis every time he/she needs to use the results. It can provide more flexible licensing, geographies and access, including controlling access by teams, specialties and access levels.

For example, a patient may come into a medical center to have a CT scan done to assess the growth of nodules in his lung. Currently, data relating to the size of his lung nodule can be collected over time, but it is difficult to put that data into context. Context in this example could be either time or population context. Advanced image processing techniques described herein can be used to measure the location, size, shape and/or volume, or other parameter of the nodules, but there is not a good way to determine the growth rate (time context) or how this patient compares to other patients with lung nodules (population context). Having access to this information could aide with diagnoses (e.g., whether the nodule is likely cancerous) and treatment (other patients with similarly growing lung nodules have responded well to medication x), among other things.

Over time, the patient image data from several geographically dispersed medical centers can be stored on a server-based system, data can be mined and analyzed to determine for example: 1) whether an aneurysm is likely to rupture based on certain quantitative characteristics of that aneurysm; 2) whether a tumor is likely to be malignant based on certain quantitative characteristics of the tumor; and 3) whether a growth is growing more quickly or more slowly than average and what that difference might mean to the patient clinically.

A clinical trial involving a new hip implant can use imaging data to determine whether the implant is remaining secure over time. The participants in this clinical trial can be geographically dispersed allowing for much more data and therefore a quicker and better study conclusion. Research around a rare type of brain tumor can advance more quickly because the imaging data can be obtained from any medical center in the world, thus allowing more of the rare patients to enroll in the study. New ways of evaluating aortic aneurysms may be discovered 10 years from now and previous imaging data can be re-analyzed retrospectively using the newly discovered information. Or, in the future, a doctor may receive a message from the cloud server saying "we have just developed the ability to detect tumors with more sensitivity and hence please be alerted that we found a possible precursor to a tumor in the scan from 5 years ago that patient X had. Follow-up recommended". If enough data can be aggregated and analyzed, the system will be able to suggest treatments for various diseases which are more likely to be successful, based on the data analysis. Standardizing analysis of patient images may be desirable if the data will be used in the aggregate. Standardized analysis tools can control what steps are done by whom or how steps are done, narrow ranges on steps, or limit steps, and pre-process on server either outside of or within users' control.

Using data mining, data may be analyzed from different perspectives and summarized into useful or relevant information. Data mining allows users to analyze data from many different dimensions or angles, categorize the data, and summarize the relationships identified. Clinical data mining may be used, for example, to identify correlations or patterns among fields in relational and/or other databases. The data mining system may include a capability to compare data across modalities and/or data sources for a particular patient, for example.

In certain embodiments, system 109 may include a portal or interface (e.g., application programming interface or API) in which information for a patient may be accessed. Once a patient is identified, a user interface is presented. The user interface includes patient demographics, current order information, current patient information (e.g., medication, allergies, chief complaint, labs, etc.), historical information (e.g., renal failure, family history, previous invasive and/or non-invasive procedures, etc.), dynamic measurement analysis, and/or configurable normal values.

The data mining system provides a dynamic snapshot of vital measurements and relevant findings across all studies in the medical data store 206 for a particular patient. The data mining system supports access to multiple data sources, cross-modality comparison, cross-data source comparisons and the like. In some embodiments, the data mining system allows data elements to be registered or subscribed so that a user, administrator and/or system setting may specify how to retrieve certain data through a variety of communications protocols (e.g., SQL, extensible markup language (XML), etc.), what functions can be applied to certain data, in which modality(ies) and/or data source(s) can a certain data element be found, whether data is enumerated and/or numeric data, etc.

Figure 4C:
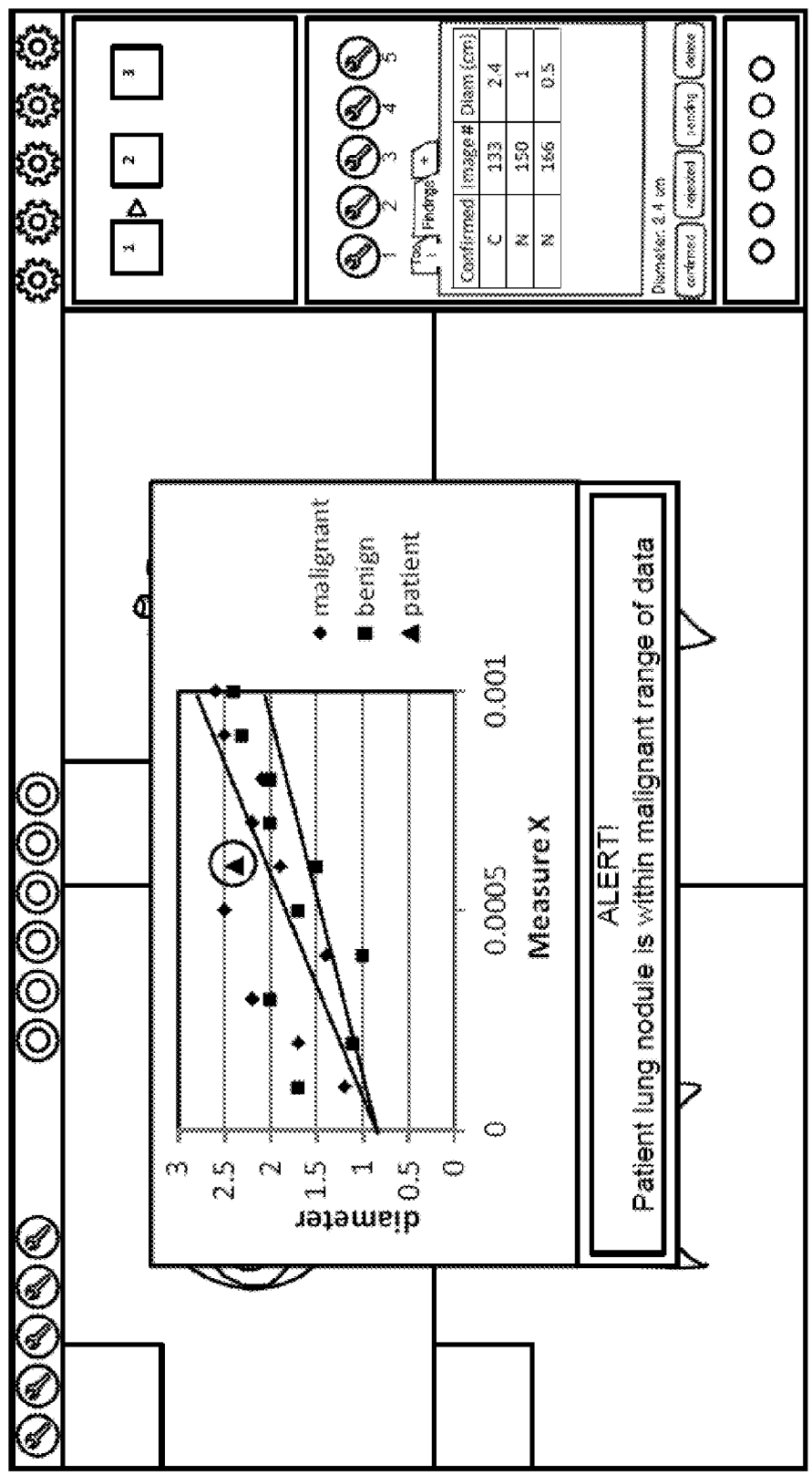

The data mining in conjunction with the system 109 helps improve efficiency by reducing steps involving users, such as medical staff, to retrieve historical data and compare findings from previous procedures. This has previously been done manually, semi-manually or not at all. The data mining system retrieves, calculates and correlates data automatically. The data mining system may provide visual indicators of data relationships along with the data. In addition, the data mining system helps providing a more efficient workflow to compare and trend data, which allows a physician or other healthcare practitioner to track disease progression and/or disease regression within the scope of evidence-based medicine. FIG. 4C is a screenshot illustrating a GUI presenting a result of data mining operations performed by a cloud server according to one embodiment of the invention. In the example represented in FIG. 4C, the current patient has a tumor, the diameter of which is represented by the triangle on the graph. The other data on the graph represent mined data of similar patients and/or similar tumors. The current patient's tumor diameter can be seen in context of the mined data. Note that in this example, an alert is displayed that says the current patient's tumor diameter is within the malignant range of data. Similar alerts would be generated depending on how the data is interpreted by the advanced image processing system.

Some embodiments provide intelligent clinical data mining. In intelligent data mining, data sets are generated based on relevant study information. The data mining system may mine data across all studies for a particular patient which includes different modalities and potentially multiple data sources. The data mining system provides real-time (or substantially real-time) analysis of vital measurements and relevant findings across all studies for a particular patient that helps improve a clinical ability to predict, diagnose and/or treat the patient.

In some embodiments, the data mining system provides interactive graphing capabilities for mined data elements. For example, a user can select different data points to be included in the graph, indicate a type of graph (e.g., line or bar), and select a size of the graph. A user may select different function(s) to be applied to a specific data element such as change or difference, average, min, max, range, etc. A user may utilize the data mining system to compare qualitative and/or quantitative data. The data mining system may be applicable to a wide variety of clinical areas and specialties, such as cardiology, disease progression and regression, evidence-based medicine, radiology, mammography (e.g., track mass growth/reduction), interventional neurology, radiology, cardiology (e.g., measure stenosis progression of carotid artery disease), hematology, oncology, etc.

In some embodiments the data mining system provides real-time or substantially real-time analysis that helps improve a clinical ability to predict, diagnose and treat. Providing better tools and better access to improved information leads to better decisions. Through trending and comparing of clinical data, the data mining system has the ability to generate graphs to give a user a visual representation of different data elements.

For example, a cardiac physician may want to review findings from previous cardiac cases in order to compare and trend relevant data. Comparing and trending the data allows the physician to track disease progression and/or disease regression. Pre-procedurally, the physician is provided with an ability to be better prepared and informed of relevant clinical data that is pertinent to an upcoming procedure. Post-procedurally, the physician is provided with an ability to compare and trend the findings within the scope of evidence-based medicine to track disease progression or regression and potentially recommend other therapies. Access to the aggregated data can also be licensed to the user separately from the use of the software itself.

Cloud-Based Medical Image Collaboration System

Referring back to FIG. 2, according to one embodiment, server 109 further includes medical image collaboration system 208 capable of hosting a medical image discussion and processing session amongst participants such as clients 202-203 discussing and processing medical images retrieved from medical data store 206 in a collaboration fashion. Each participant can participate (e.g., view and/or modify images) in the discussion to a certain degree dependent upon his/her respective access privileges controlled by access control system 210. Different participants may participate in different stages of a discussion session or a workflow process of the images. Dependent upon the access or user privileges associated with their roles (e.g., doctors, insurance agents, patients, or third party data analysts or researchers), different participants may be limited to access only a portion of the information relating to the images or processing tools without compromising the privacy of the patients associated with the images. Participants may also communicate with each other in a collaborative manner, including via chat, instant messaging, voice or other means. This communication may be in either real time or recorded.

Figure 5:
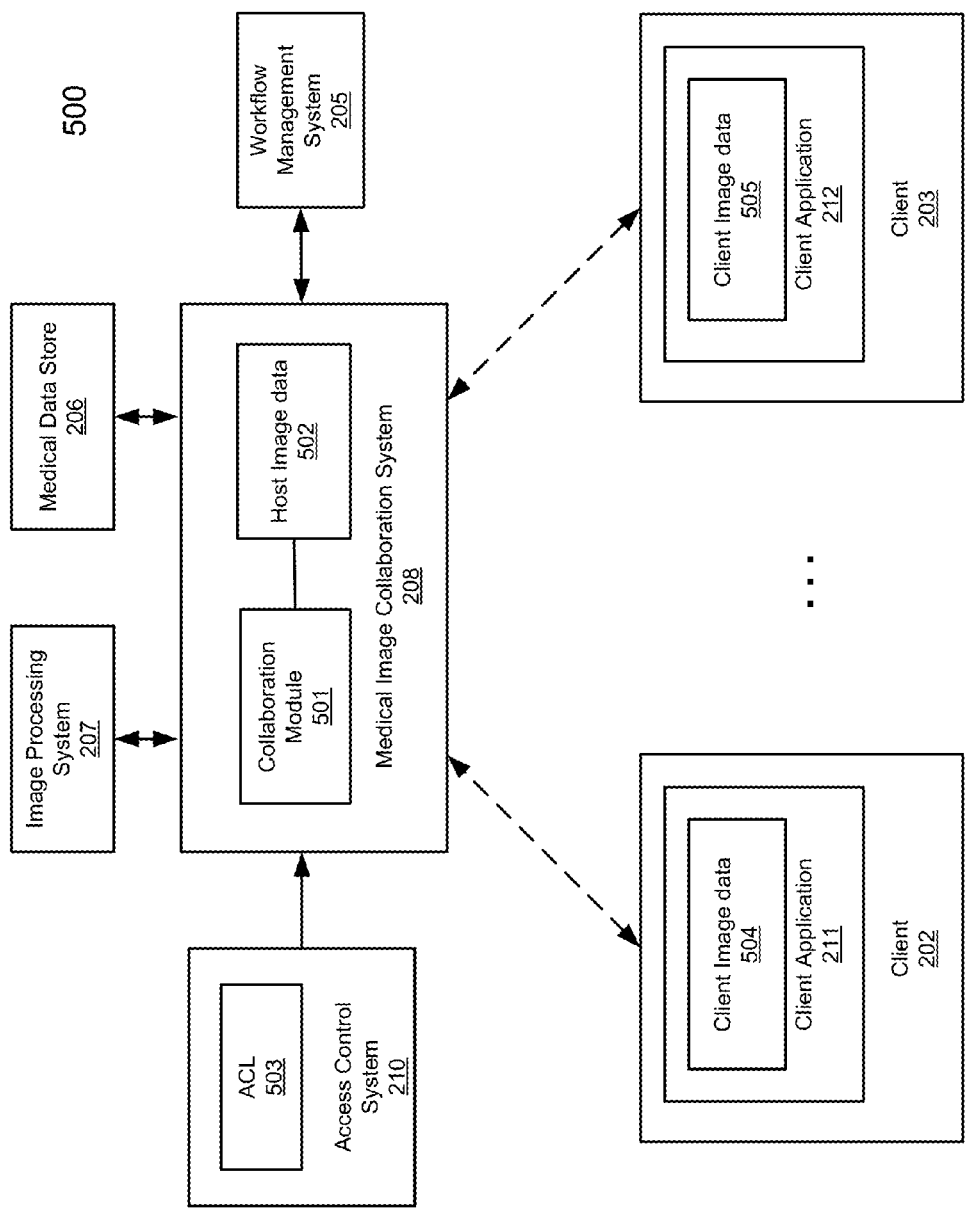
FIG. 5 is a block diagram illustrating a cloud-based image collaboration system according to one embodiment of the invention.

FIG. 5 is a block diagram illustrating a cloud-based image collaboration system according to one embodiment of the invention. Referring to FIG. 5, system 500 includes a medical image collaboration system 208 configured to host a discussion and processing forum in the cloud concerning a medical image, which is accessible by clients 202-203 in a collaborated manner from anywhere in the world through the Internet. In one embodiment, collaboration system 208 includes a collaboration module 501 to coordinate communications and actions amongst clients 202-203 discussing, viewing and/or manipulating host image and/or image data 502. In response to an image manipulation or rendering command received from one of clients 202-203 on image 502, collaboration module 501 is configured to invoke image processing system 207 to render image 502 according to the command. Collaboration module 501 is configured to update image and/or image data 502 based on the rendering result received from image processing system 207.

In addition, collaboration module 501 generates, via image processing system 207, client images and/or image data 504-505 and transmits client images and/or image data 504-505 to clients 202-203, respectively. Client images and/or image data 504-505 may be viewed based on access privileges (e.g., part of access control list or ACL 503) of clients 202-203. Certain information associated with host image and/or image data 502 may not be visible based on the access privileges of clients 202-203. For example, if a user of client 202 is an auditor, client image 504 may not include patient information, based on the ACL as shown in FIG. 3B. However, if a user of client 203 is a physician, client image 505 may include the patient information based on the ACL as shown in FIG. 3B. Note that throughout this application, a client image referred to herein represents a client image file or files that may include the actual image (e.g., same or similar to the host image) and other associated data such as metadata (e.g., DICOM tags or headers), description or notes of the image, and/or access control data configuring client applications during processing the image, etc. In one embodiment, GUIs or controls for invoking certain graphics rendering tools to manipulate host image and/or image data 502 via the corresponding client images 504-505 may or may not be enabled or available at client applications 211-212 dependent upon the access privileges of users associated with clients 202-203, such as the one shown in FIG. 3A. Furthermore, host image and/or image data 502 may be part of a particular stage of a workflow process managed by workflow management system 205. Some of clients 202-203 may participate in one stage and others may participate in another stage dependent upon the corresponding ACL such as the one shown in FIG. 3C. In one embodiment, collaboration module 501 is configured to coordinate the image processing stages amongst clients 202-203. When a first client has completed one stage, collaboration module 501 may send a notification to a second client such that the second client can take over the control of the image data and processing the image data of the next stage, etc.

Figure 6A:
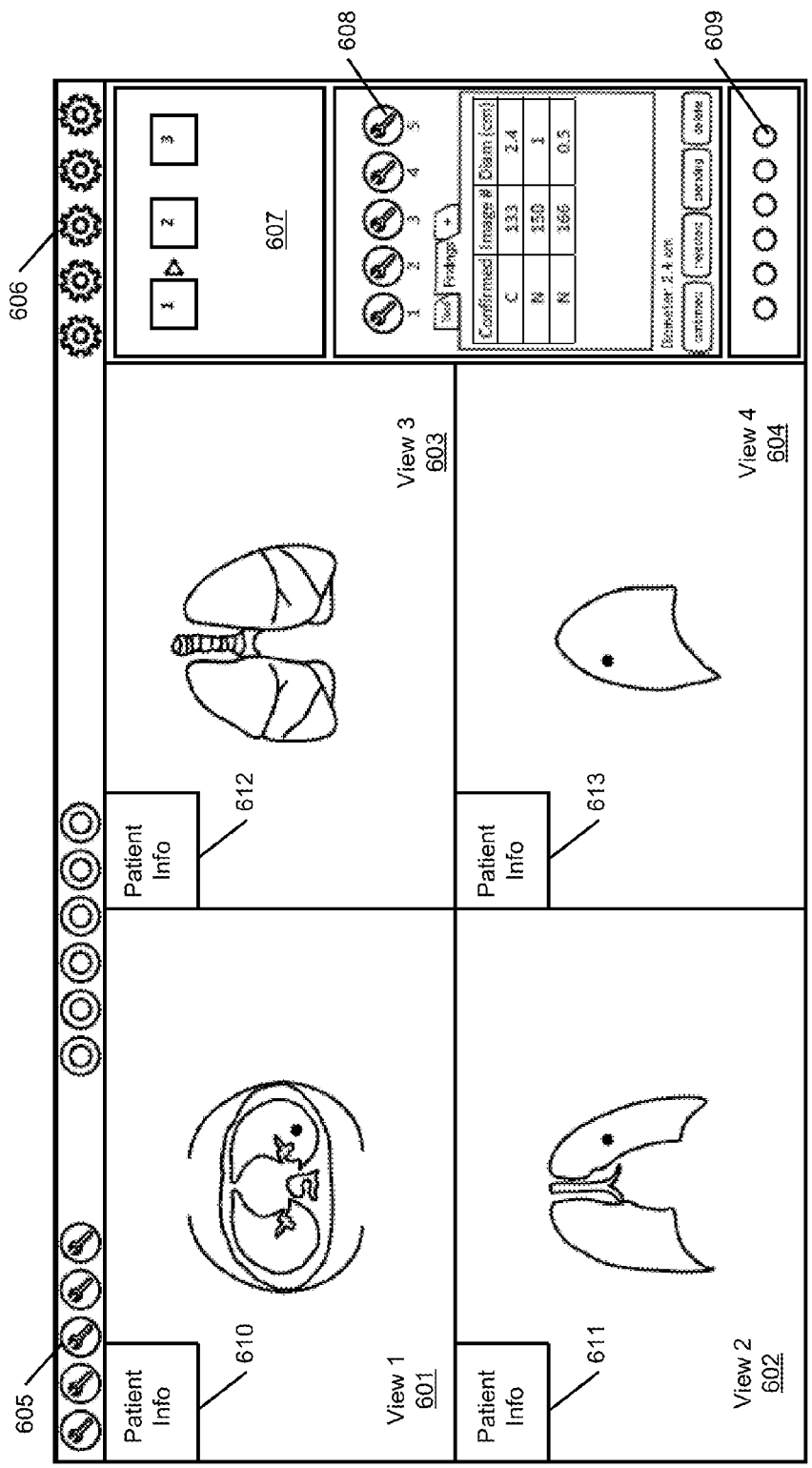
FIGS. 6A-6D are screenshots illustrating certain GUIs of a medical image collaboration system according certain embodiments of the invention.
Figure 6B:
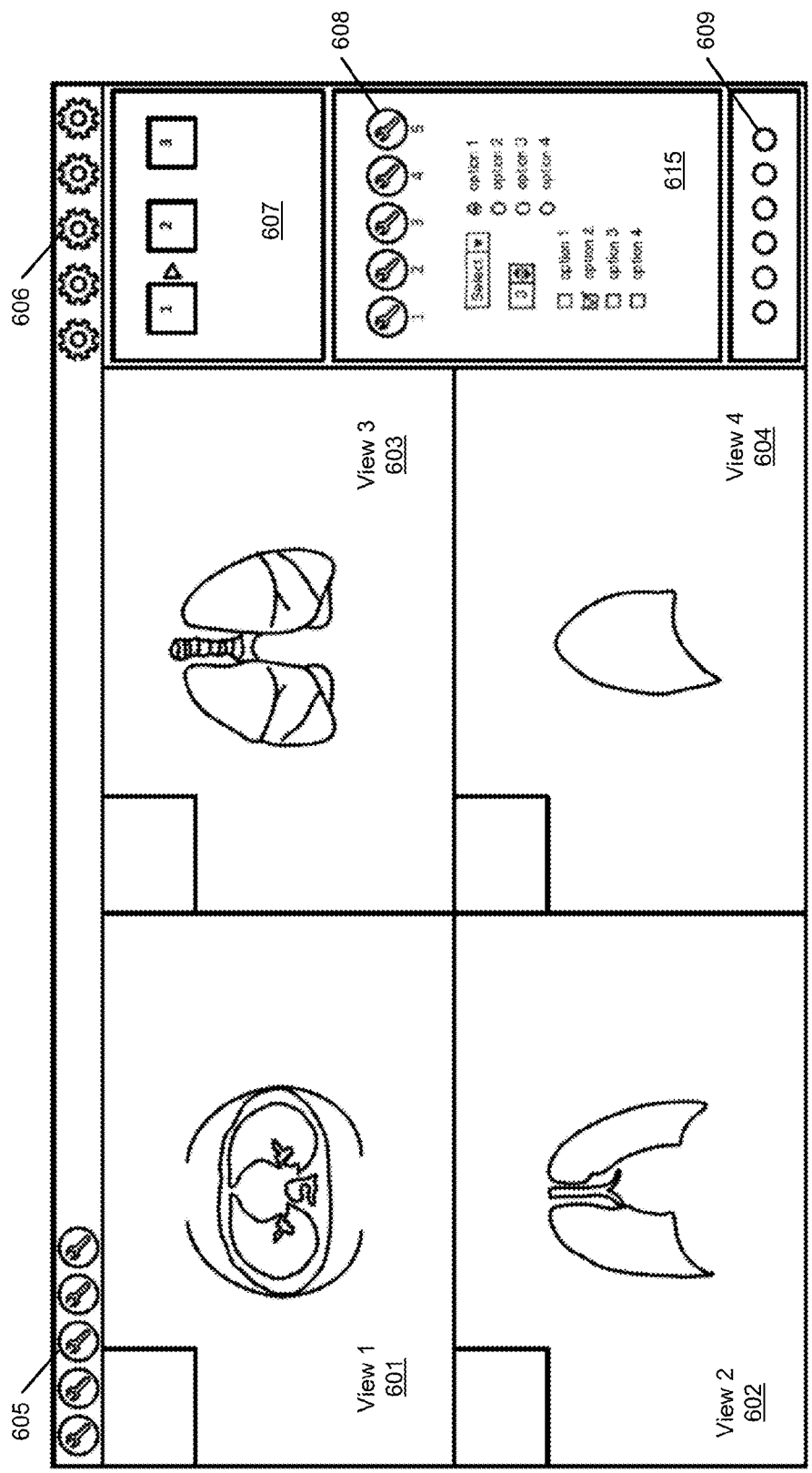
Figure 6C:
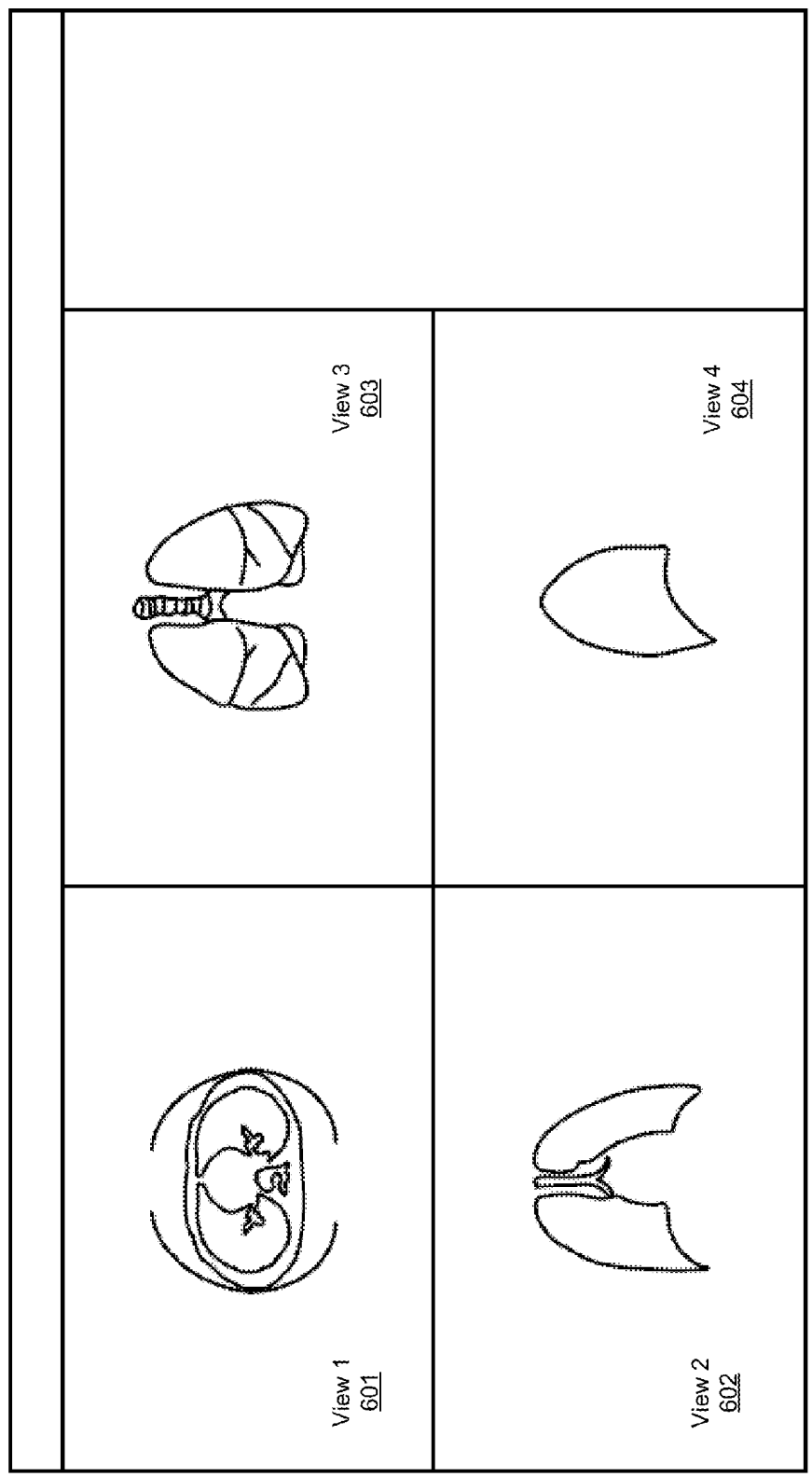
Figure 6D:
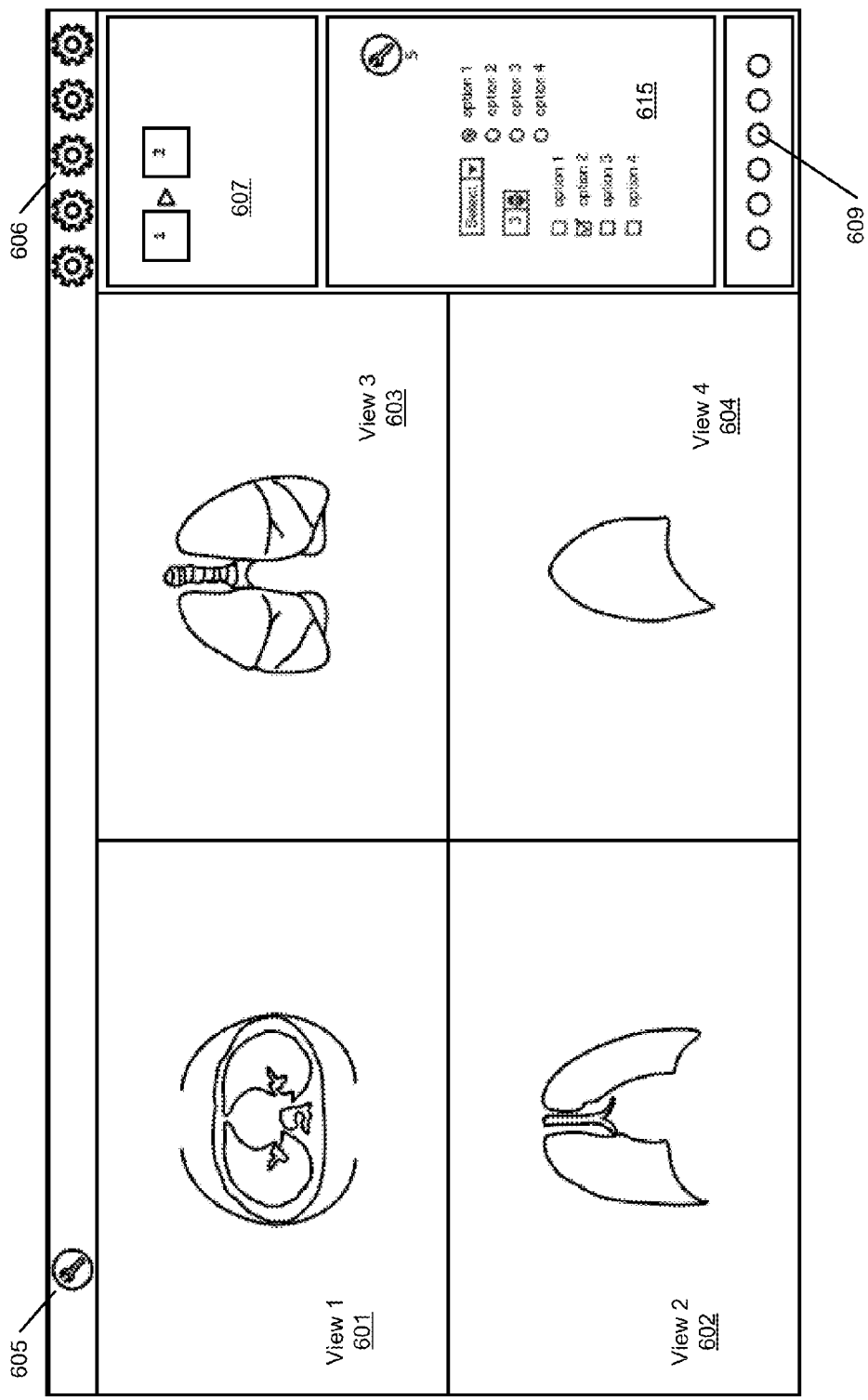

FIGS. 6A-6D are screenshots illustrating certain GUIs of a medical image collaboration system according to certain embodiments of the invention. GUIs of FIGS. 6A-6D may be presented by a client application (e.g., thin client) of various clients operated by various users. For example, FIG. 6A represents a GUI page by a client application operated by a user that has a high level of access privileges. Referring to FIG. 6A, in this example, the user can view most of the information presented by the image collaboration system including most of the image processing tools 605 and 608 that can be utilized to manipulate images and/or image data 601-604, settings 606, workflow templates 607, image viewing tools 609, such as different orientations (anterior, head, posterior, right, foot, left), different views (axial, sagittal, coronal), different screen orientations, etc.], and patient information 610-613. FIG. 6B represents a GUI page that can be viewed by another user. Referring to FIG. 6B, this user may not have the necessary privileges to view the patient information. As a result, the patient information is not displayed. FIG. 6C represent a GUI in which a user can only view the image without the capability of manipulating the images. FIG. 6D represent a GUI in which a user has a limited capability of manipulating the images and/or image data.

Figure 7:
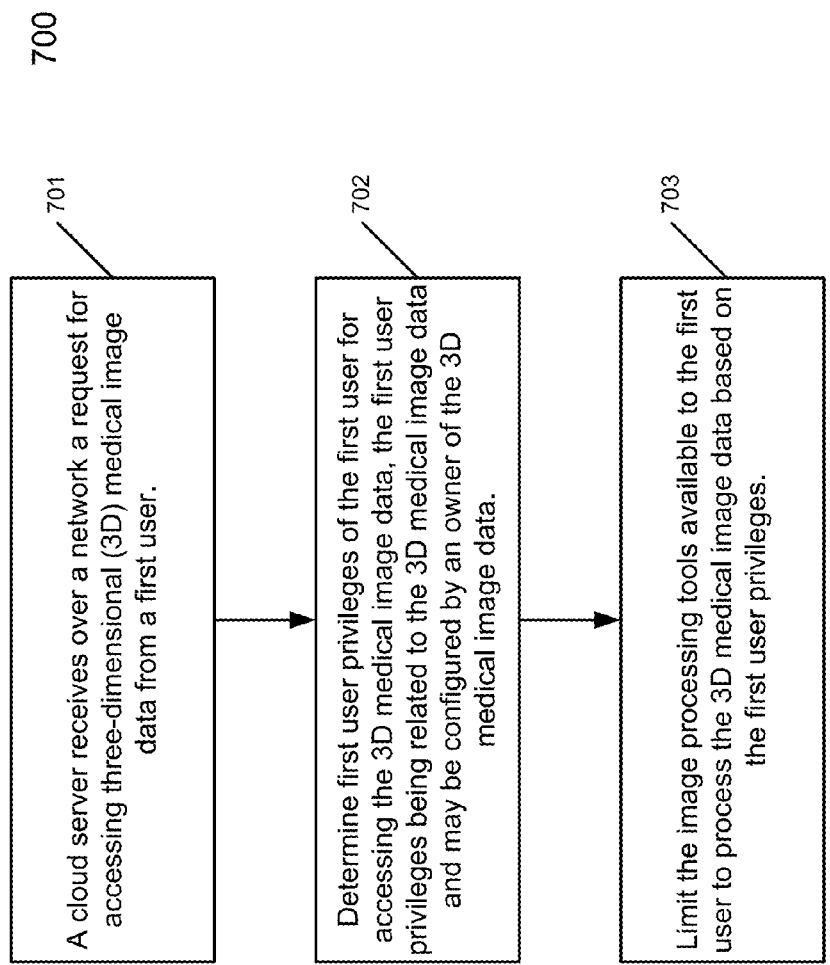
FIG. 7 is a flow diagram illustrating a method for processing medical images in a collaboration environment according to one embodiment of the invention.

FIG. 7 is a flow diagram illustrating a method for processing medical image data according to one embodiment of the invention. Method 700 may be performed by cloud server 109 of FIG. 1. Referring to FIG. 7, at block 701, a cloud server receives over a network a request for accessing three-dimensional (3D) medical image data from a first user. The cloud server provides image processing services to a variety of users over the network such as the Internet. At block 702, the cloud server determines first user privileges of the first user for accessing the 3D medical image data. The first user privileges may be related to the 3D medical image data and may be configured by an owner of the 3D medical image data. Based on the first user privileges, the cloud server is configured to limit the image processing tools available to the first user to process the 3D medical image data.

Figure 8:
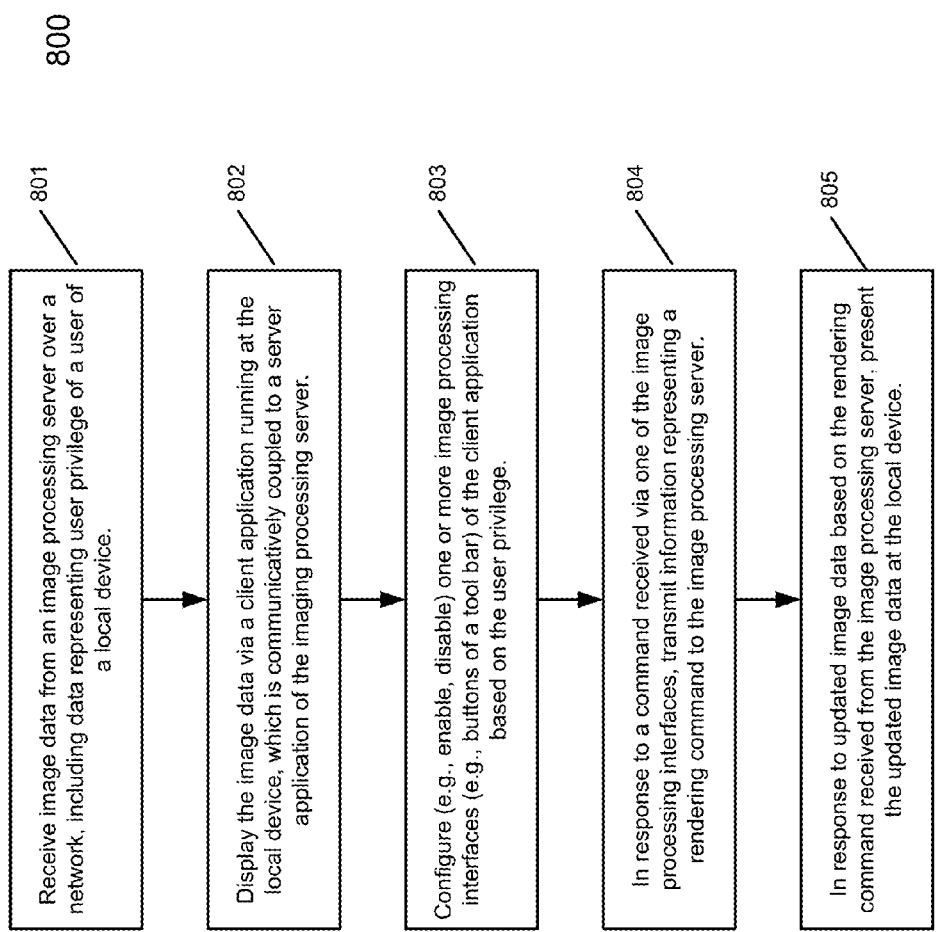
FIG. 8 is a flow diagram illustrating a method for processing medical images in a collaboration environment according to another embodiment of the invention.

FIG. 8 is a flow diagram illustrating a method for processing medical image data in a collaboration environment according to another embodiment of the invention. Method 800 may be performed by a client application such as client applications 211-212 of FIG. 5. Referring to FIG. 8, at block 801, image data is received at a client from an image processing cloud server over a network, including information relating to user privileges of a user of the client device. At block 802, the image data is displayed via a client application running at the client device. At block 803, one or more image processing interfaces (e.g., buttons of a toolbar) of the client application is configured (e.g., enabled/activated or disabled/deactivated) based on the user privileges. In response to a command received via one of the enabled image processing interface, information representing a rendering command is transmitted to the image processing server over the network. In response to updated image data received from the image processing server, the updated image data is represented at the local client device. This type of access control may occur with or without conferencing.

Conferencing/collaboration includes more than one user looking at and/or using the advanced imaging software for a particular study, image or series of images as services provided by a cloud at the same time or at different times. This might include a physician consulting with a patient in another location, or a physician consulting with another physician, or other users. One user may be using the software to manipulate, measure, analyze images while other user(s) observe. More than one user may be actively using the software at the same time. Another example of collaboration is when more than one user is contributing to a case or cases at different times. For example one physician may perform certain steps or stages relating to patient image data, such as the bone removal step, and then another physician might perform different steps at a later time, such as vessel identification/labeling and/or measurement. Another user might review and validate certain previously performed steps, etc.

A cloud-based software system allows conferencing/collaboration to be done on a level not possible before, using the techniques described throughout this application. Since the software and the data reside centrally (e.g., a single server, server farm or redundant servers), it is simply a matter of providing access to image data and access to the advanced image processing software. The image data may relate to a subset of one procedure, one patient, or more than one patient/procedure. The software and image data can be accessed from anywhere and at any time, by anybody whom has been provided access, without extensive software are hardware installation. There are several situations where it would be desirable to have more than one user access the images and data relating to a procedure, patient or group of patients.

One such situation is when a user seeks a second opinion. For example, a patient, or physician, or insurer, may want to obtain a second opinion concerning a procedure, patient or group of patients. By allowing more than one physician access to the images and data of a case, a user (e.g., patient, physician, insurer, etc.) may request and obtain more than one opinion concerning the case. The physicians may access the data at different times, or at the same time. Each physician may want to view the steps and views that the other physician went through to come up with his or her diagnosis/conclusion. So not only would two physicians be able to view the same case at either the same time or different times, but one or more of the physicians, or other users, may be able to view a record of the steps that the other physician went through to come up with his or her conclusion. In this scenario, users may simultaneously or independently utilize the software. Different access privileges may be applied to different users.

Similar to the second opinion situation, a patient, physician or insurer may desire the opinion of an expert in a particular field. For example, a patient may receive a heart scan which reveals a rare condition. The patient, his/her physician and/or insurer may request the opinion of an expert in the field of that rare condition. Similar to the second opinion scenario, the users may view and manipulate, measure etc. the images of the case simultaneously; user history can be tracked as in the second opinion scenario. In this scenario, users may simultaneously or independently utilize the software.

In certain cases, for example in the case of a clinical trial, the United States Food and Drug Administration (FDA) may want to monitor the progress and results. In this case, an individual or individuals at the FDA would be a user and may want to observe or monitor other users using the software to view or manipulate images and/or data. The representative from the FDA may also be interested in looking at anonymous aggregated data. FDA users may only need to view the anonymous data without the option of manipulating the data.

In another example, a representative from an insurer may want to monitor the results from a patient or group of patients or doctor(s). In this case, an individual or individuals at the insurer would be a user and would observe or monitor the results of other users using the software. The representative from the insurer may also be interested in looking at anonymous aggregated data. Insurance users may only need to view the anonymous data without the option of manipulating the data. They may use the information for billing purposes or cost reductions/discounts.

Another potential use for collaborative advanced imaging software is during a procedure, such as a surgical procedure. For example, a surgeon in a rural town may want the help of an expert at a major medical center. Collaborative use of the software in the actual operating room would allow the surgeon to benefit from the guidance of the expert in real time. The expert could also help plan the surgical procedure beforehand using the advanced imaging software collaboratively. As with any of the embodiments, different access privileges may be applied to different users.

In another scenario, a medical center might outsource all or part of its advanced image processing operations to an outside company. Or it might outsource only certain types of cases. Or it might outsource certain steps in cases which are more complex. The usage of the software can be licensed in a variety of licensing models. A patient may control the process—this opens up the opportunity for patients to have more control over their care. For example, the patient might control a username and password for their case which they can then give to anyone, including a second opinion doctor, etc. The username and password may be temporary, expiring after a configured time frame or a number of uses or other parameter. Different users such as doctors or technicians, or experts can do different steps or stages in image processing, for example, in a workflow process.

Training is another scenario in which the conferencing and collaboration can be utilized. In a training environment, there tends to be a large number of users. Some features of a testing environment include testing, lectures, certification and others. In a testing situation, several users will use the advanced image processing software to view and manipulate or analyze image data on the same case or different cases, either simultaneously, or independently. Test scoring can be performed automatically, or by an instructor viewing the result and process of the various students. The results may be quantitative or qualitative. In a lecture situation, there may be a need to present cases to students in a fairly controlled manner, by limiting what the students can see on any given case, or by magnifying certain aspects of a case for closer viewing and/or emphasis. In some situations, there may be a need to have the same case presented in two windows on the student's computer so that the student can see what the instructor is doing in one window, but can also use the advanced imaging software independently on the same case in the other window. There may be a need to certify a user to do certain types of cases using the advanced image processing software or to use certain aspects of the advanced image processing software. This would involve a fairly structured course with a test or tests which must be passed in order for the user to be certified. This type of training could be done live, or as an online course which is self-paced.

Traditionally, advanced image processing software has been used primarily by radiologists. This is largely because radiologists have access to the workstation with the software installed at the medical center. But other physicians and technicians in other specialties, such as cardiology, orthopedics, dentistry, neurology, pathology, etc., would also benefit from using this type of advanced image processing system. Since the cloud-based system effectively eliminates the need for expensive and extensive hardware and software installation and maintenance, access to advanced image processing software in the cloud becomes possible for any type of physician or technician, whether or not he/she is associated with a medical institution. An individual physician in private practice can use the software at even its most advanced level immediately and without up-front costs and installation delays.

Since advanced image processing software is complex, training may be required before a user is proficient using the software. However, different levels of software can be created for different user levels. A "dumbed down" version, which does not include the more complex tools, can be created for basic users, such as a primary care physician. More advanced versions of the software can be created for more advanced users such as radiologists who have been trained to use the more advanced tools. Different specialties can also have different versions of the software. For example, cardiologist may only need and want access to the advanced image processing tools relating to the heart.

Cloud-Based Medical Data Anonymous Gateway Management

In order to truly use advanced image processing software in a cloud model, it is necessary to receive the slice image data from the modality, or scanner, onto a server in the cloud. Different types of medical image capturing devices include CT, MRI, PET, single photon emission computed tomography (SPECT), ultrasound, tomography, etc. Traditionally, the lack of efficient and effective methods for moving large volumes of image data has prevented the transition from workstation and server-based systems to a cloud-based system. In the past, fewer scans were performed and there were fewer image slices per scan. The volume of data is increasing quickly creating the need for an easy way of transferring significant numbers of large images efficiently and without extensive setup.

Currently, most image data is transferred from a medical image capturing device to a PACS system. A PACS system generally exists at a medical institution behind a firewall to protect the data. The existence of a firewall can make the transfer of files in either direction challenging because of security policies and rules. A virtual private network (VPN) has been used to transfer files, but installation of a VPN requires extensive involvement from the hospital or medical centers IT department to make sure that all security policies are considered and that the system integrates seamlessly with their current system. For this reason, the setup of a VPN is time consuming, unpredictable, and sometimes impossible or impractical.

According to some embodiments, a cloud-based medical image processing system includes a data gateway manager to automatically transfer medical data to/from data providers such as medical institutes. Such data gateway management may be performed based on a set of rules or policies, which may be configured by an administrator or authorized personnel. In one embodiment, in response to updates of medical image data during an image discussion session or image processing operations performed at the cloud, the data gateway manager is configured to transmit over a network (e.g., Internet) the updated image data or the difference between the updated image data and the original image data to a data provider that provided the original medical images. Similarly, the data gateway manager is configured to transmit any new images from the data provider. In addition, the data gateway manager may further transfer data amongst multiple data providers that is associated with the same entity (e.g., multiple facilities of a medical institute). Furthermore, the cloud-based system may automatically perform certain pre-processing operations of the received image data using certain advanced image processing resources provided by the cloud systems.

Figure 9:
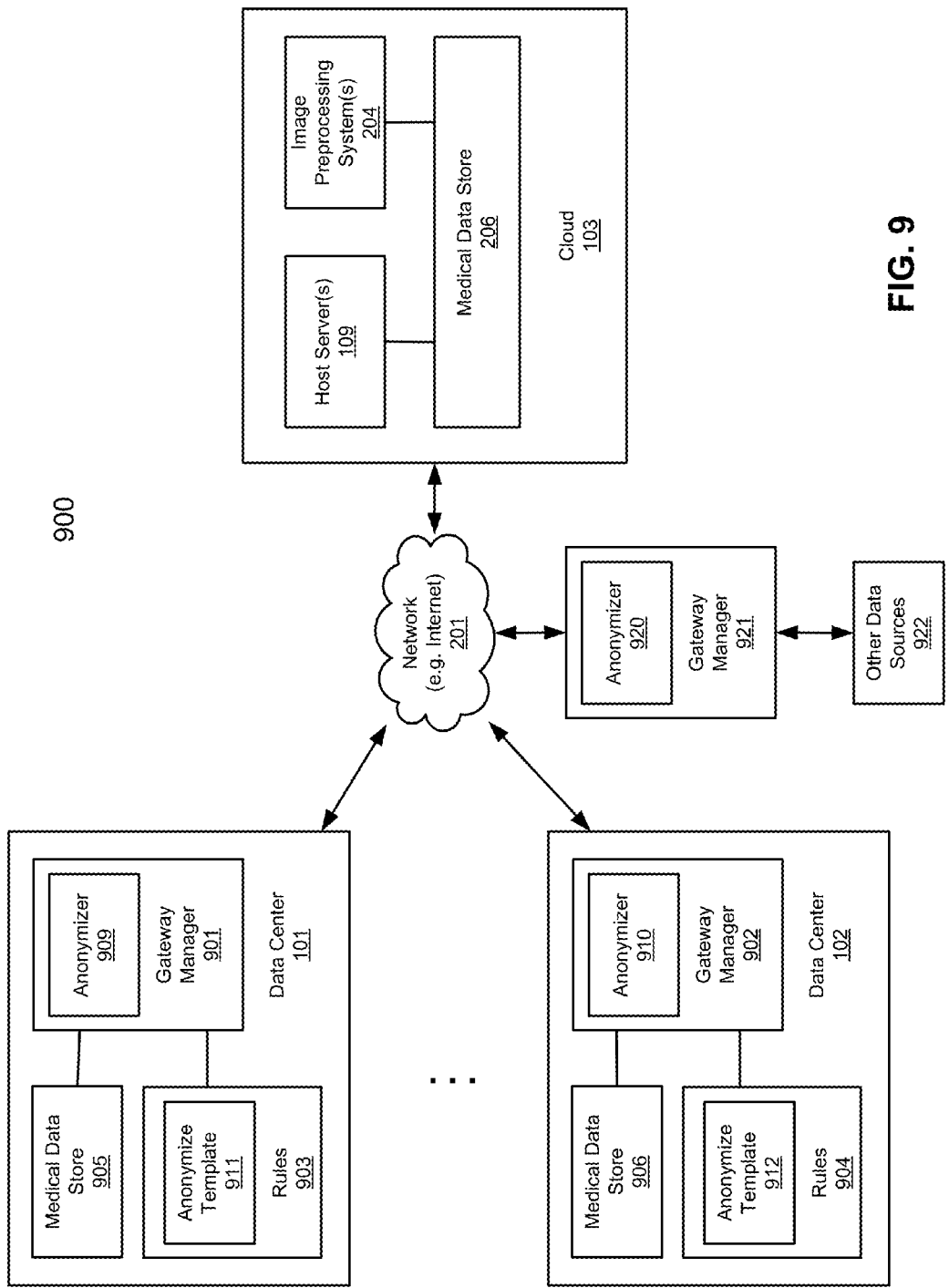
FIG. 9 is a block diagram illustrating a cloud-based image processing system according to another embodiment of the invention.

FIG. 9 is a block diagram illustrating a cloud-based image processing system according to another embodiment of the invention. Referring to FIG. 9, system 900 includes cloud 103 having one or more cloud servers 109 to provide image processing services to a variety of clients for processing images stored in medical data store 206. Image data stored in data store 206 may be received over network 201 (e.g., Internet) from a variety of data sources such as data centers 101-102. Server 109 may include some or all of the functionalities described above. Each of data centers 101-102 includes a data store such as data stores 905-906 to store or archive medical image data captured by a variety of image capturing devices, such as CT, MRI, PET, SPECT, ultrasound, tomography, etc. The data centers 101-102 may be associated with different organization entities such as medical institutes. Alternatively, data centers 101-102 may be associated with different facilities of the same organization entity.

In one embodiment, each of data centers 101-102 includes a data gateway manager (also referred to as an uploader and/or downloader) such as data gateway managers 901-902 to communicate with cloud 103 to transfer medical data amongst data stores 905-906 and 206, respectively. Data gateway managers 901-902 can communicate with the cloud server according to a variety of communications protocols, such as hypertext transfer protocol secure (HTTPS) (e.g., HTTP with transport layer security/secure sockets layer (TLS/SSL)), etc., using a variety of encryption and/or compression techniques.

In one embodiment, for the purpose of illustration, when new image data is received from an image capturing device and stored in data store 905, data gateway manager 901 is configured to automatically transmit the new image data to cloud 103 to be stored in data store 206. The new image data may be transmitted to cloud 103 and stored in a specific area or directory of data store 206 based on the configuration or profile set forth in a set of rules 903. Rules 903 may be configured by a user or an administrator via an API such as a Web interface. Similarly, if new or updated image data is received from a user and stored in data store 206, for example, during a Web conferencing session, data gateway manager 907 may be configured to automatically transmit the new or updated image data to data center 101 according to a set of rules 903, which may also be configured by a user or administrator. According to some embodiments, data gateway managers 901-902 may also communicate with each other to transfer data stored in data stores 905-906, particularly, when data centers 101-102 are associated with the same organization, or associated in some other way, as in a clinical or research trial.

According to one embodiment, each of data gateway managers 901-902 includes a data anonymizer such as anonymizers 909-910, prior to transmitting medical data to cloud 103 or amongst data centers 101-102, configured to anonymize certain information from the medical data, such as patient information including, but is not limited to, patient name, address, social security number, credit card information, etc. Such an anonymization can be performed based on rules which are preconfigured, or configured at the time of data transfer and/or in an anonymization configuration file (e.g., anonymization configuration files 911-912), which can be configured by a user or an administrator via an administration user interface associated with the data gateway manager. Note that data gateway management may also be performed with other data sources 922 (e.g., image storage systems, CD-ROMS, computer hard drives etc.) via the respective data gateway manager 921 and anonymizer 920.

According to some embodiments, the data gateway managers 901-902 allow a user (e.g., clinic, hospital, private practice, physician, insurer, etc.) to easily, and in some cases, automatically, upload image data (and/or other data) to server 109 and stored in medical data store 206 in cloud 103. The data gateway manager can be configured using a Web browser interface, where the configuration may be stored as a set of rules 903-904 or the rules can be determined at the time of data transfer by a user. Certain internet ports such as ports 80 and 443 can be used for such data transfers. Using these protocols allows the user (institution, hospital etc.) to use ports and protocols that in most cases are already set up for secure transfer of data without setting up a separate VPN.

The Web interface allows a user to configure the file transfer using a Web browser. This can be done each time image data is transferred to the cloud, or can be set up to automatically upload certain image data, cases or portions of cases based on rules. Some examples of rules can be configured based on modality, patient, dates, doctors, times, flags, clinical trial qualifications, multiple criteria, etc. Generally, patient identifying data needs to be removed from the image data before they are transferred or during transfer. This is referred to as 'anonymization." This can be done in a number of ways and can also be automated using rules such as based on birth date, upload date, institution, etc.

The anonymization can be done in a number of ways including, but not limited to, blanking or masking out characters in the DICOM header, replacing characters in the DICOM header with non-identifying characters, substitution, encryption, transformation, etc. Depending on the anonymization methods, de-anonymization, or partial de-anonymization, may be possible. For example in a clinical trial, if a patient is experiencing unacceptable side effects, it would be desirable to de-anonymize their clinical trial data to determine whether the patient was taking a placebo or a drug. The access control would be necessary so that only those users with certain privileges would be allowed to de-anonymize the data.

Figure 10A:
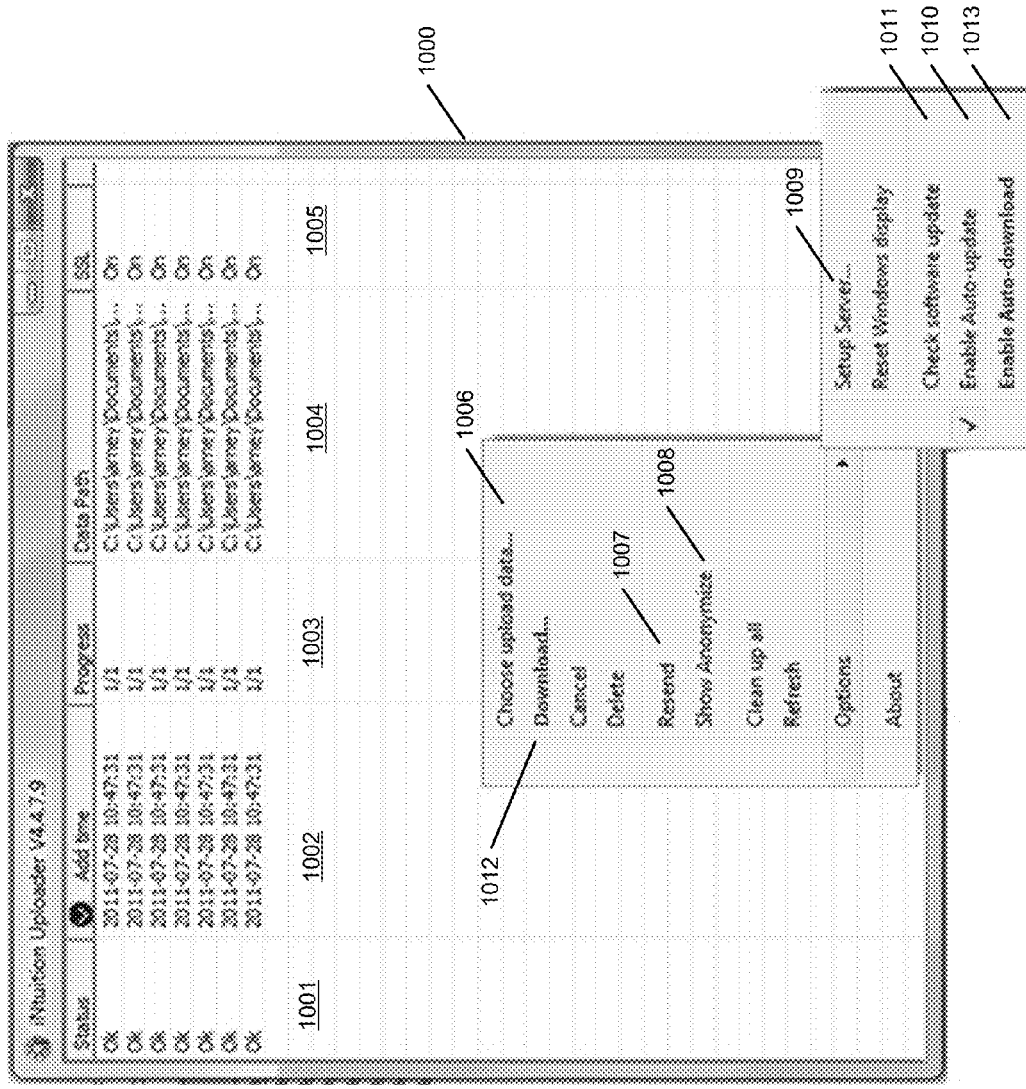
FIGS. 10A and 10B are screenshot illustrating examples of graphical user interfaces for configuring data gateway management according to certain embodiments of the invention.
Figure 10B:
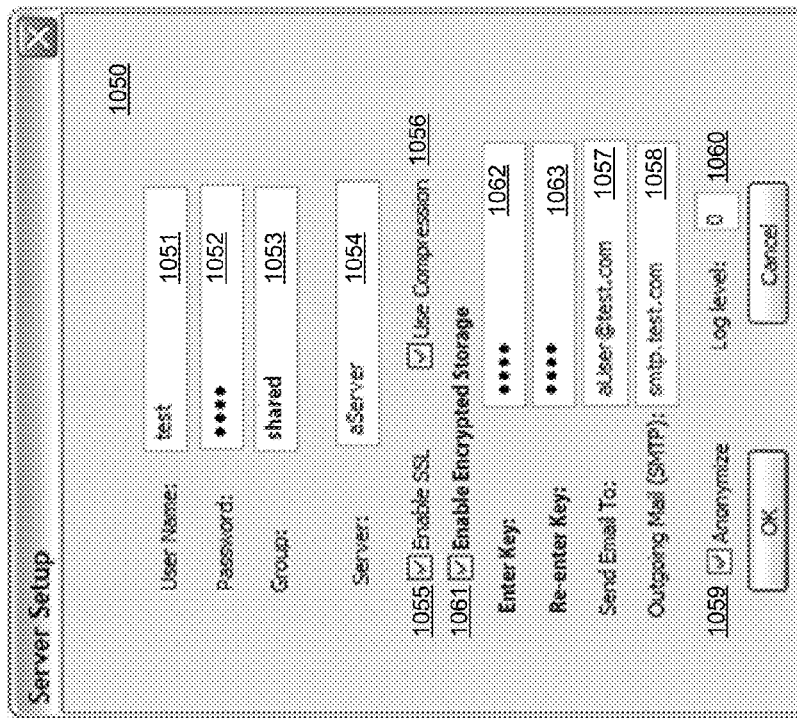

FIGS. 10A and 10B are screenshots illustrating examples of graphical user interfaces for configuring the gateway manager according to certain embodiments of the invention. For example, the GUIs as shown in FIGS. 10A and 10B may be presented by client applications 211-212 of FIG. 2, which may be a client application or Web browser interface. The GUI for the gateway manager may also be an application separate from client applications 211-212. Referring to FIG. 10A, in one embodiment, GUI 1000 allows a user to configure the data files to be transferred to/from a server such as server 109 of FIG. 2. A user can add one or more files into the GUI 1000 via link 1006 or alternatively, by drag-and-dropping one or more individual files and/or a folder of files into GUI 1000. Each file to be transmitted to/from the server is associated with an entry shown in GUI 1000. Each entry includes, but is not limited, status field indicating a file transfer status, time field 1002 indicating the time when the file was added, progress indication 1003, source data path 1004 from which the file is retrieved, and security indicator 1005 indicating whether the transfer is conducted in a secure manner, etc.

Figure 12A:
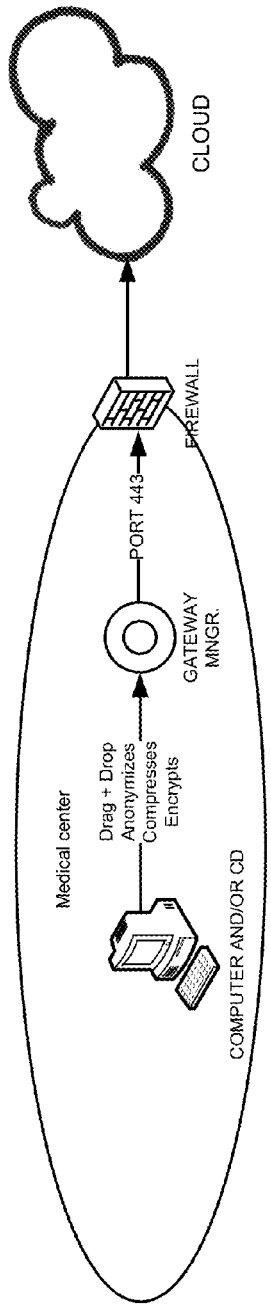
FIGS. 12A-12C are block diagrams illustrating certain system configurations according to some embodiments of the invention.
Figure 12B:
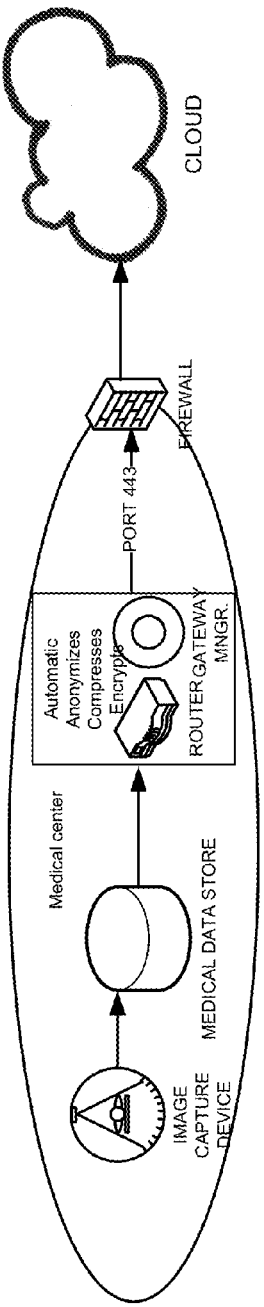
Figure 12C:
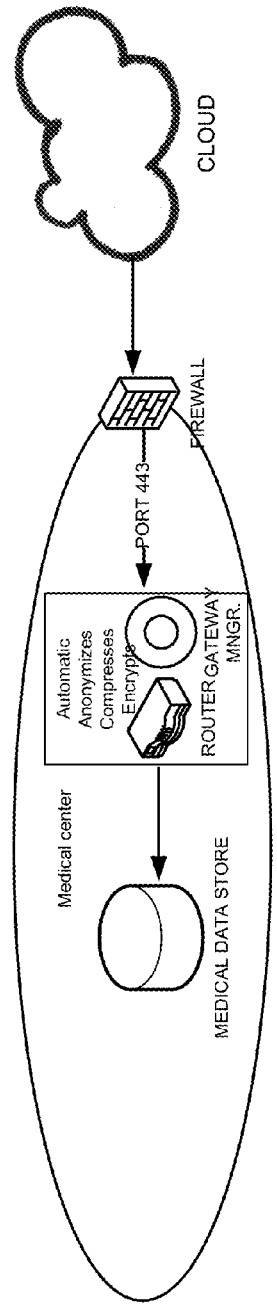

A file can be manually selected, for example, by drag-and-dropping the file into a specific folder. The file is then anonymized, compressed, and/or encrypted, and uploaded to the cloud, as shown in FIG. 12A. Alternatively, a router and/or gateway manager can be configured to automatically upload to the cloud, with optional anonymization, compression, and/or encryption, image data captured by an imaging device and stored in a medical data store, as shown in FIG. 12B. Furthermore, a router and/or gateway manager can also be configured to automatically download from the cloud, with optional anonymization, compression, and/or encryption, image data and to store the image data in a medical data store, as shown in FIG. 12C. The protocol used for transferring data may be a DICOM transmission protocol or other appropriate protocol or protocols. DICOM transmission protocol may use the following TCP and UDP port numbers: Port 104 is a well-known port for DICOM over TCP or UDP. Since port 104 is in the reserved subset, many operating systems require special privileges to use it. Port 2761 is a registered port for DICOM using Integrated Secure Communication Layer (ISCL) over TCP or UDP. Port 2762 is a registered port for DICOM using Transport Layer Security (TLS) over TCP or UDP. Port 11112 is a registered port for DICOM using standard, open communication over TCP or UDP.

Once files associated with a study have been uploaded to the cloud server, the user may be able to see a list which studies are in that account (not shown). The list identifies the status of the studies and/or files, including whether it has been downloaded previously and/or whether it has been read or changed. The user has the option of automatically or manually downloading any changed studies which have not been previously downloaded, or choosing which studies to download. The user also has the option of showing only studies that have been changed and not downloaded in the account or sort the list so that the non-downloaded studies are listed at the top of the list. When files and/or studies are specified for download, either automatically via link 1013 or manually via link 1012, the files/studies can be downloaded to a specific location in a local computer hard drive and/or the files/studies can be downloaded to a non-local computer hard drive.

According to one embodiment, a file whose transfer fails due to an error can be resent via link 1007. An alert can also be sent via email, displayed on a screen pop-up or added to a database for listing. The software associated with GUI 1000 may be automatically updated via link 1010 or manually updated via link 2011. The destination or server to receive the files can also be configured via link 1009. When link 1009 is activated, GUI 1050 is presented as shown in FIG. 10B. Referring now to FIG. 10B, in GUI 1050, a user can specify the username via field 1051 and password in field 1052 to access the server specified via field 1054. The user can also specify a group or directory to which the file or files to be transferred via field 1053. The user can also specify whether a secured connection is needed via field or checkbox 1055 and a data compression method is utilized via field or checkbox 1056. Compression can be either lossless or lossy. Further, the user can provide an email address via field 1057 and the email system via field 1058 to allow the system to send an email to the user regarding the data transfer. The user can also specify whether the data will be anonymized via field or checkbox 1059, as well, as the data logging detailed level via field 1060. Furthermore, a user can specify by enabling checkbox 1061 that the data is to be stored in an encrypted form. The user can also provide a key via fields 1062-1063 to a recipient to decrypt the data.

Figure 11:
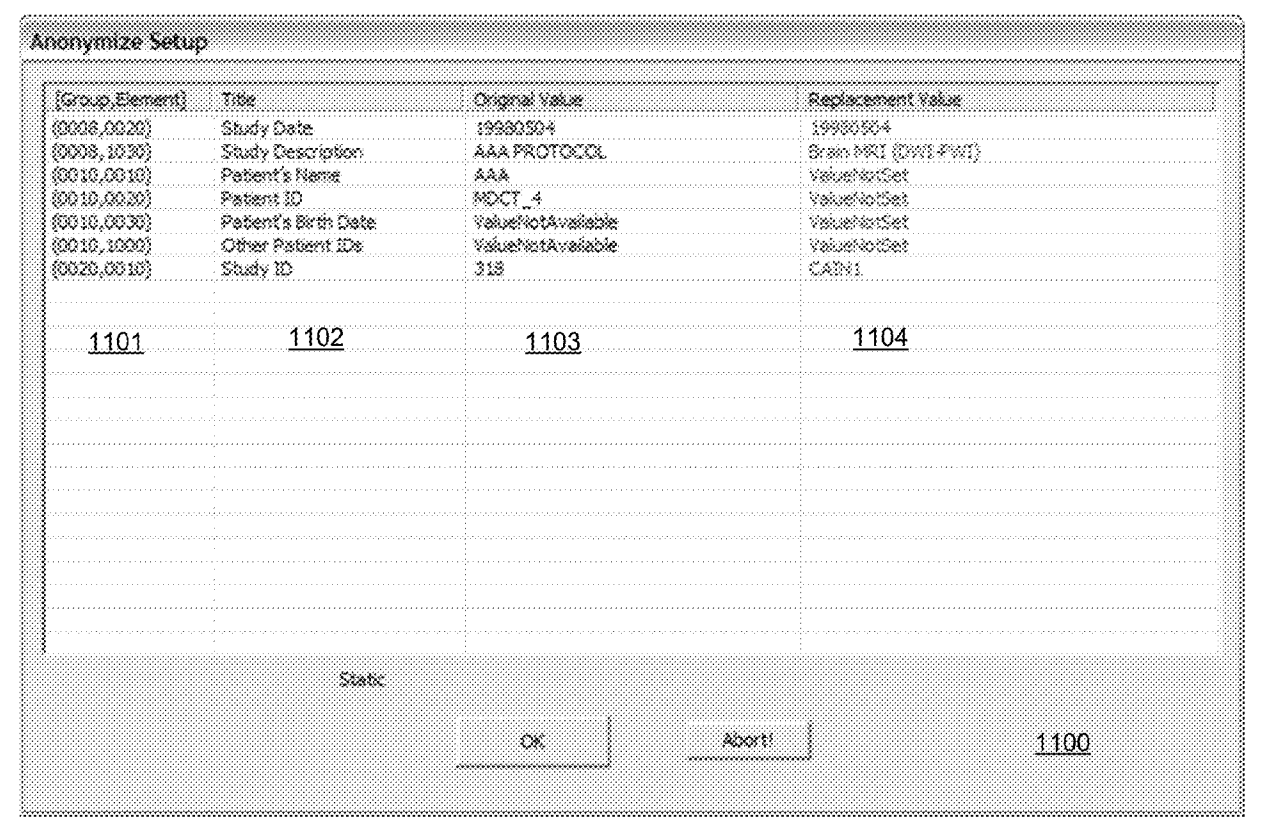

FIG. 11 is a screenshot illustrating examples of GUIs for configuring anonymous data gateway management according to certain embodiments of the invention. GUI 1100 can be presented by activating link 1008 of FIG. 10A. Referring to FIG. 11, GUI 1100 allows a user to specify items to be anonymized, where each item is specified in one of the entries listed in GUI 1100. Each item is referenced by its DICOM tag 1101, name 1102, original value 1103 to be replaced, and replacement value 1104 to replace the corresponding original value. In this example, a user can set the new value by clicking column 1104 and enter the new value. If the DICOM tag is a date type, a date selector will be displayed to allow the user to select the date. If the values allowed are predefined, a drop down list is displayed for selecting one of the predefined values or strings. If there is a mask defined for the tag, a masked edit GUI is displayed to allow the user to change the value according to the displayed mask. The user input maybe examined by the system based on the type of the DICOM tag. If the information is incorrect, the user may be prompted to reenter the correct value. After all user inputs are collected, a new anonymous template or configuration file is created and stored. Note that the GUIs as shown in FIGS. 10A-10B and 11 can be presented and operated via a variety of user interactions such as keystrokes, clicking, touching, voice interactive commands, or a combination thereof. Also note that the formats or configurations of the GUIs in FIGS. 10A-10B and 11 are described for the purpose of illustration only; other formats or layouts may also be utilized. The GUI may be in the form of a browser or a phone or other mobile device application.

Figure 13:
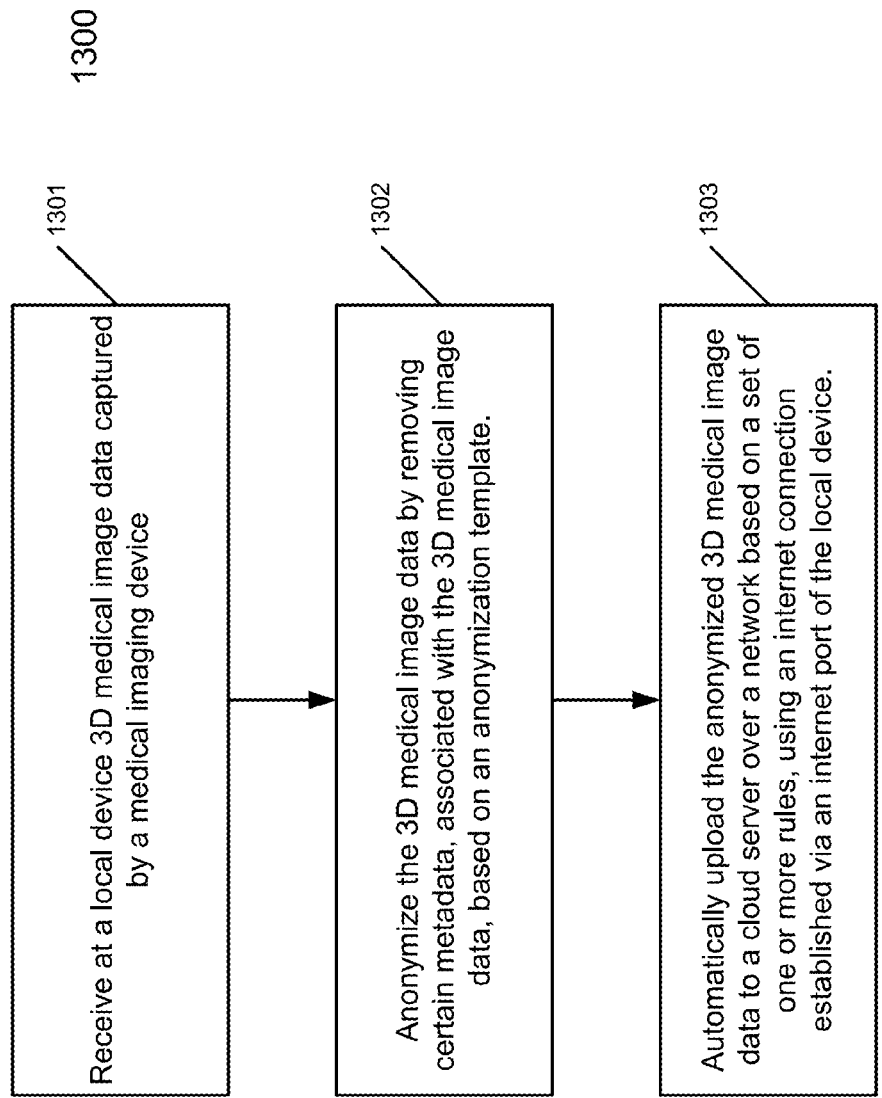
FIG. 13 is a flow diagram illustrating a method for anonymizing medical data according to another embodiment of the invention.

FIG. 13 is a flow diagram illustrating a method for anonymizing medical data according to another embodiment of the invention. Method 1300 may be performed by any of data gateway managers 901-902, 921 of FIG. 9. Referring to FIG. 13, at block 1301, a local device (e.g., gateway manager/router/computer) receives a 3D medical image data captured by a medical imaging device. At block 1302, the 3D medical image data is anonymized including removing certain metadata associated with the 3D medical image data based on an anonymization template. At block 1303, the anonymized 3D medical image data is then automatically uploaded to a cloud server, using a network connection established via an internet port of the local device.

Applications of Cloud-Based Services

The embodiments described above can be applied to a variety of medical areas. For example, the techniques described above can be applied to vessel analysis (including Endovascular Aortic Repair (EVAR) and electrophysiology (EP) planning). Such vessel analysis is performed for interpretation of both coronary and general vessel analysis such as carotid and renal arteries, in addition to aortic endograft and electro-physiology planning. Tools provided as cloud services include auto-centerline extraction, straightened view, diameter and length measurements, Curved Planar Reformation (CPR) and axial renderings, as well as charting of the vessel diameter vs. distance and cross-sectional views. The vessel track tool provides a Maximum Intensity Projection (MIP) view in two orthogonal planes that travels along and rotates about the vessel centerline for ease of navigation and deep interrogation. Plaque analysis tools provide detailed delineation of non luminal structure such as soft plaque, calcified plaque and intra-mural lesions.

In addition, the techniques described above can be utilized in the area of endovascular aortic repair. According to some embodiments, vascular analysis tools provided as cloud services support definition of report templates which captures measurements for endograft sizing. Multiple centerlines can be extracted to allow for planning of EVAR procedures with multiple access points. Diameters perpendicular to the vessel may be measured along with distances along the two aorto-iliac paths. Custom workflow templates may be used to enable the major aortic endograft manufactures' measurement specifications to be made as required for stent sizing. Sac segmentation and volume determination with a "clock-face" overlay to aid with documenting the orientation and location of branch vessels for fenestrated and branch device planning, may also be used. Reports containing required measurements and data may be generated.

The techniques described above can also be applied in the left atrium analysis mode, in which semi-automated left atrium segmentation of each pulmonary vein ostium is supported with a single-click distance pair tool, provided as cloud services, for assessment of the major and minor vein diameter. Measurements are automatically detected and captured into the integrated reporting system. These capabilities can be combined with other vessel analysis tools to provide a comprehensive and customized EP planning workflow for ablation and lead approach planning.

The techniques described above can also be utilized in calcium scoring. Semi-automated identification of coronary calcium is supported with Agatston, volume and mineral mass algorithms being totaled and reported on-screen. Results may be stored in an open-format database along with various other data relating to the patient and their cardiovascular history and risk factors. A customized report can be automatically generated, as part of cloud services, based upon these data. Also includes report generation as defined by the Society of Cardiovascular Computed Tomography (SCCT) guidelines.

The techniques described above can also be utilized in a time-volume analysis (TVA), which may include fully-automated calculation of left ventricular volume, ejection fraction, myocardial volume (mass) and wall thickening from multi-phasic data. A fast and efficient workflow provided as part of cloud services allows for easy verification or adjustment of levels and contours. The results are presented within the integrated reporting function.

The techniques described above can also be utilized in the area of segmentation analysis and tracking (SAT), which includes supports analysis and characterization of masses and structures in various scans, including pulmonary CT examinations. Features include single-click segmentation of masses, manual editing tools to resolve segmentation issues, automatic reporting of dimensions and volume, graphical 3D display of selected regions, integrated automated reporting tool, support for follow-up comparisons including percent volume change and doubling time, and support for review of sphericity filter results.

The techniques described above can also be utilized in the area of flythrough which may include features of automatic segmentation and centerline extraction of the colon, with editing tools available to redefine these centerlines if necessary. 2D review includes side-by-side synchronized supine and prone data sets in either axial, coronal or sagittal views with representative synchronized endoluminal views. 3D review includes axial, coronal and sagittal MPR or MIP image display with large endoluminal view and an unfolded view that displays the entire colon. Coverage tracking is supported to ensure 100% coverage with stepwise review of unviewed sections, one-click polyp identification, bookmark and merge findings, as well as a cube view for isolating a volume of interest and an integrated contextual reporting tool. Support is provided for use of sphericity filter results.

The techniques described above can also be utilized in the area of time-dependent analysis (TDA), which provides assessment tools for analyzing the time-dependent behavior of appropriate computerized tomographic angiography (CTA) and/or MRI examinations, such as within cerebral perfusion studies. Features include support for loading multiple time-dependent series at the same time, and a procedural workflow for selecting input and output function and regions of interest. An integrated reporting tool is provided as well as the ability to export the blood flow, blood volume and transit time maps to DICOM. The tools may also be used with time-dependent MR acquisitions to calculate various time-dependent parameters.

The techniques described above can also be utilized in the area of CTA-CT subtraction, which includes automatic registration of pre- and post-contrast images, followed by subtraction or dense-voxel masking technique which removes high-intensity structures (like bone and surgical clips) from the CTA scan without increasing noise, and leaving contrast-enhanced vascular structures intact.

The techniques described above can also be utilized in dental analysis, which provides a CPR tool which can be applied for review of dental CT scans, offering the ability to generate "panoramic" projections in various planes and of various thicknesses, and cross-sectional MPR views at set increments along the defined curve plane.

The techniques described above can also be utilized in the area of multi-phase MR (basic, e.g. breast, prostate MR). Certain MR examinations (for example, breast, prostate MR) involve a series of image acquisitions taken over a period of time, where certain structures become enhanced over time relative to other structures. This module features the ability to subtract a pre-enhancement image from all post-enhancement images to emphasize visualization of enhancing structures (for example, vascular structures and other enhancing tissue). Time-dependent region-of-interest tools are provided to plot time-intensity graphs of a given region.

The techniques described above can also be utilized in parametric mapping (e.g. for multi-phase Breast MR), in which the parametric mapping module pre-calculates overlay maps where each pixel in an image is color-coded depending on the time-dependent behavior of the pixel intensity. The techniques described above can also be utilized in the area of SphereFinder (e.g. sphericity filter for lung and colon). SphereFinder pre-processes datasets as soon as they are received and applies filters to detect sphere-like structures. This is often used with lung or colon CT scans to identify potential areas of interest. The techniques described can also be utilized in fusion for CT/MR/PET/SPECT. Any two CT, PET, MR or SPECT series, or any two-series combination can be overlaid with one assigned a semi-transparent color coding and the other shown in grayscale and volume rendering for anatomical reference. Automatic registration is provided and subtraction to a temporary series or to a saved, third series is possible.

The techniques described above can also be utilized in the area of Lobular Decomposition. Lobular Decomposition is an analysis and segmentation tool that is designed with anatomical structures in mind. For any structure or organ region which is intertwined with a tree-like structure (such as an arterial and/or venous tree), the Lobular Decomposition tool allows the user to select the volume of interest, as well as the trees related to it, and to partition the volume into lobes or territories which are most proximal to the tree or any specific sub-branch thereof. This generic and flexible tool has potential research applications in analysis of the liver, lung, heart and various other organs and pathological structures.

The techniques described above can also be utilized in the area of Volumetric Histogram. Volumetric Histogram supports analysis of a given volume of interest based on partition of the constituent voxels into populations of different intensity or density ranges. This can be used, for example, to support research into disease processes such as cancer (where it is desirable to analyze the composition of tumors, in an attempt to understand the balance between active tumor, necrotic tissue, and edema), or emphysema (where the population of low-attenuation voxels in a lung CT examination may be a meaningful indicator of early disease).

The techniques described above can also be utilized in the area of Motion Analytics. Motion Analytics provides a powerful 2D representation of a 4D process, for more effective communication of findings when interactive 3D or 4D display is not available. Any dynamic volume acquisition, such as a beating heart, can be subjected to the Motion Analysis, to generate a color-coded "trail" of outlines of key boundaries, throughout the dynamic sequence, allowing a single 2D frame to capture and illustrate the motion, in a manner that can be readily reported in literature. The uniformity of the color pattern, or lack thereof, reflects the extent to which motion is harmonic, providing immediate visual feedback from a single image.

The techniques described above can also be utilized to support other areas such as Multi-KV, enhanced multi-modality, findings workflow, and iGENTLE available from TeraRecon. Multi-KV: Support for Dual Energy and Spectral Imaging provides support for established applications of dual energy or spectral imaging CT data, such as removal of bone or contrast, as well as toolkits to support research and investigation of new applications of such imaging techniques. Enhanced multi-modality support is offered, including support for PET/MR fusion, and improved applications for MR such as time-intensity analysis and parametric mapping tools, which may be applied in the study of perfusion characteristics of normal or cancerous tissue.

Findings Workflow supports progressive analysis of serial acquisitions, for the same patient. Each finding can be tracked across multiple examinations, in a table that is maintained indefinitely in the iNtuition system's database, without requiring the prior scans to remain present on the system. Measurement data and key images are captured and retained, allowing new scans to be placed in context with prior results, and reports to be produced at any time. Support for RECIST 1.1 is included although the tool may readily be used for analysis of various progressive conditions, not only those related to oncology. Export using the AIM (Annotation and Image Markup) XML Schema is supported.

iGENTLE ensures that iNtuition's powerful suite of segmentation, centerline, and metadata extraction tools continue to work effectively, even with noisy scans characterized by low-dose acquisitions. Metadata are extracted from enhanced copies of the original scan, and then applied back onto the original, unmodified data, to improve performance of 3D tools without denying access to the original scan data.

Example of Data Processing System

FIG. 14 is a block diagram of a data processing system, which may be used with one embodiment of the invention. For example, the system 1400 may be used as part of a server or a client as shown in FIG. 1. Note that while FIG. 14 illustrates various components of a computer system, it is not intended to represent any particular architecture or manner of interconnecting the components; as such details are not germane to the present invention. It will also be appreciated that network computers, handheld computers, cell phones and other data processing systems which have fewer components or perhaps more components may also be used with the present invention.

As shown in FIG. 14, the computer system 1400, which is a form of a data processing system, includes a bus or interconnect 1402 which is coupled to one or more microprocessors 1403 and a ROM 1407, a volatile RAM 1405, and a non-volatile memory 1406. The microprocessor 1403 is coupled to cache memory 1404. The bus 1402 interconnects these various components together and also interconnects these components 1403, 1407, 1405, and 1406 to a display controller and display device 1408, as well as to input/output (I/O) devices 1410, which may be mice, keyboards, modems, network interfaces, printers, and other devices which are well-known in the art.

Typically, the input/output devices 1410 are coupled to the system through input/output controllers 1409. The volatile RAM 1405 is typically implemented as dynamic RAM (DRAM) which requires power continuously in order to refresh or maintain the data in the memory. The non-volatile memory 1406 is typically a magnetic hard drive, a magnetic optical drive, an optical drive, or a DVD RAM or other type of memory system which maintains data even after power is removed from the system. Typically, the non-volatile memory will also be a random access memory, although this is not required.

While FIG. 14 shows that the non-volatile memory is a local device coupled directly to the rest of the components in the data processing system, the present invention may utilize a non-volatile memory which is remote from the system; such as, a network storage device which is coupled to the data processing system through a network interface such as a modem or Ethernet interface. The bus 1402 may include one or more buses connected to each other through various bridges, controllers, and/or adapters, as is well-known in the art. In one embodiment, the I/O controller 1409 includes a USB (Universal Serial Bus) adapter for controlling USB peripherals. Alternatively, I/O controller 1409 may include an IEEE-1394 adapter, also known as FireWire adapter, for controlling FireWire devices.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as those set forth in the claims below, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The techniques shown in the figures can be implemented using code and data stored and executed on one or more electronic devices. Such electronic devices store and communicate (internally and/or with other electronic devices over a network) code and data using computer-readable media, such as non-transitory computer-readable storage media (e.g., magnetic disks; optical disks; random access memory; read only memory; flash memory devices; phase-change memory) and transitory computer-readable transmission media (e.g., electrical, optical, acoustical or other form of propagated signals—such as carrier waves, infrared signals, digital signals).

The processes or methods depicted in the preceding figures may be performed by processing logic that comprises hardware (e.g. circuitry, dedicated logic, etc.), firmware, software (e.g., embodied on a non-transitory computer readable medium), or a combination of both. Although the processes or methods are described above in terms of some sequential operations, it should be appreciated that some of the operations described may be performed in a different order. Moreover, some operations may be performed in parallel rather than sequentially.

In the foregoing specification, embodiments of the invention have been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A computer-implemented method for providing cloud-based image processing services, the method comprising:
   receiving, at a cloud server over a network, a request for accessing medical image data from an application running at a client device used by a user, the cloud server providing image processing services to a plurality of users in a plurality of image processing steps provided by the cloud server, resulting in a plurality of image views;
   determining, by an access control system hosted by the cloud server, user privileges of the user for accessing the medical image data, wherein the medical image data was captured by a medical imaging device and stored in a storage associated with the cloud server;
   in response to receiving a command from the application of the client device, the command having a selection of one or more of image views available to the user, providing by the cloud server the medical image data based on the selected one or more image views provided by the cloud server;
   tracking, by a tracking system hosted by the cloud server, user interactions of the user with the medical image data via the selected image views, including tracking how much time the user takes to complete a particular medical image processing step, wherein tracking user interaction further comprises tracking billing information of the user associated with usage of the image processing steps;
   storing the tracked user interactions in a persistent storage, wherein the persistent storage is configured to track and store user interactions of a plurality of users at the cloud server; and
   performing, by a data mining system hosted by the cloud server, an analysis on the tracked user interactions stored in the persistent storage to determine an overall usage trend of the image views.

2. The method of claim 1, wherein tracking user interaction comprises recording user activities of the user with the medical image data in view of the user privileges.

3. The method of claim 2, wherein tracking user interaction further comprises recording which of a plurality of medical image data processing steps the user has interacted with.

4. The method of claim 2, wherein tracking user interaction further comprises recording a user type of the user, which is one of an expert user, a regular user, a technician, and a physician.

5. The method of claim 1, wherein the medical image data is part of an electronic health record (EHR) of a patient received from an EHR provider over the network.

6. The method of claim 5, wherein the application running at a client device is medical client software integrated with EHR client software, and wherein the medical client software concurrently accesses the EHR record at an EHR server associated with the EHT provider without having to specifically launch a separate application.

7. The method of claim 6, wherein the EHR record and the medical image data are identified by a patient identifier (ID) identifying the patient at the EHR server and the cloud server, respectively.

8. A non-transitory machine-readable medium having executable instructions stored therein, which when executed by a processor, cause the processor to perform operations for providing cloud-based image processing services, the operations comprising:
   receiving, at a cloud server over a network, a request for accessing medical image data from an application running at a client device used by a user, the cloud server providing image processing services to a plurality of users in a plurality of image processing steps provided by the cloud server, resulting in a plurality of image views;
   determining user privileges of the user for accessing the medical image data, wherein the medical image data was captured by a medical imaging device and stored in a storage associated with the cloud server;
   in response to receiving a command from the application of the client device, the command having a selection of one or more of image views available to the user, providing by the cloud server the medical image data based on the selected one or more image views provided by the cloud server;
   tracking user interactions of the user with the medical image data via the selected image views, including tracking how much time the user takes to complete a particular medical image processing step, wherein tracking user interaction further comprises tracking billing information of the user associated with usage of the image processing steps;
   storing the tracked user interactions in a persistent storage, wherein the persistent storage is configured to track and store user interactions of a plurality of users at the cloud server; and
   performing an analysis on the tracked user interactions stored in the persistent storage to determine an overall usage trend of the image views.

9. The non-transitory machine-readable medium of claim 8, wherein tracking user interaction comprises recording user activities of the user with the medical image data in view of the user privileges.

10. The non-transitory machine-readable medium of claim 9, wherein tracking user interaction further comprises recording which of a plurality of medical image data processing steps the user has interacted with.

11. The non-transitory machine-readable medium of claim 9, wherein tracking user interaction further comprises recording a user type of the user, which is one of an expert user, a regular user, a technician, and a physician.

12. The non-transitory machine-readable medium of claim 8, wherein the medical image data is part of an electronic health record (EHR) of a patient received from an EHR provider over the network.

13. The non-transitory machine-readable medium of claim 12, wherein the application running at a client device is medical client software integrated with EHR client software, and wherein the medical client software concurrently accesses the EHR record at an EHR server associated with the EHT provider without having to specifically launch a separate application.

14. The non-transitory machine-readable medium of claim 13, wherein the EHR record and the medical image data are identified by a patient identifier (ID) identifying the patient at the EHR server and the cloud server, respectively.

15. A data processing system, comprising:
   a processor; and
   a memory coupled to the processor to store instructions, which when executed from the memory, cause the processor to perform operations, the operations including
      receiving, at a cloud server over a network, a request for accessing medical image data from an application running at a client device used by a user, the cloud server providing image processing services to a plurality of users in a plurality of image processing steps provided by the cloud server, resulting in a plurality of image views,
      determining user privileges of the user for accessing the medical image data, wherein the medical image data was captured by a medical imaging device and stored in a storage associated with the cloud server,
      in response to receiving a command from the application of the client device, the command having a selection of one or more of image views available to the user, providing by the cloud server the medical image data based on the selected one or more image views provided by the cloud server,
      tracking user interactions of the user with the medical image data via the selected image views, including tracking how much time the user takes to complete a particular medical image processing step, wherein tracking user interaction further comprises tracking billing information of the user associated with usage of the image processing steps,
      storing the tracked user interactions in a persistent storage, wherein the persistent storage is configured to track and store user interactions of a plurality of users at the cloud server, and
      performing an analysis on the tracked user interactions stored in the persistent storage to determine an overall usage trend of the image views.

16. The system of claim 15, wherein tracking user interaction comprises recording user activities of the user with the medical image data in view of the user privileges.

17. The system of claim 16, wherein tracking user interaction further comprises recording which of a plurality of medical image data processing steps the user has interacted with.

* * * * *